US010858679B2

(12) United States Patent
Figge et al.

(10) Patent No.: US 10,858,679 B2
(45) Date of Patent: Dec. 8, 2020

(54) INCREASING METHIONINE YIELD

(71) Applicant: METABOLIC EXPLORER, Saint Beauzire (FR)

(72) Inventors: Rainer Figge, Riom (FR); Philippe Soucaille, Deyme (FR); Guillaume Barbier, Clermont Ferrand (FR); Gwénaëlle Bestel-Corre, Saint Beauzire (FR); Cédric Boisart, Chamaliere (FR); Michel Chateau, Riom (FR)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/043,138

(22) Filed: Feb. 12, 2016

(65) Prior Publication Data

US 2016/0160249 A1 Jun. 9, 2016

Related U.S. Application Data

(63) Continuation of application No. 12/681,177, filed as application No. PCT/EP2008/062859 on Sep. 25, 2008, now abandoned.

(30) Foreign Application Priority Data

Oct. 2, 2007 (WO) ................ PCT/EP2007/060433

(51) Int. Cl.
*C12P 13/12* (2006.01)
*C12N 9/80* (2006.01)
(52) U.S. Cl.
CPC ............... *C12P 13/12* (2013.01); *C12N 9/80* (2013.01); *C12Y 305/0101* (2013.01)
(58) Field of Classification Search
CPC .................................. C12P 13/12; C12N 9/80
See application file for complete search history.

(56) References Cited

U.S. PATENT DOCUMENTS

2006/0270013 A1\* 11/2006 Chateau .................. C12N 15/47

FOREIGN PATENT DOCUMENTS

| EP | 0798916 A1 | 9/1997 |
| KR | 10-2006-0011345 A | 2/2006 |
| WO | WO 99/27107 A2 | 6/1999 |
| WO | WO 2006/001616 A1 | 1/2006 |
| WO | WO 2006/082254 A2 | 8/2006 |
| WO | WO 2007/020295 | 2/2007 |
| WO | WO 2007/077041 A1 | 7/2007 |
| WO | WO 2008/101857 A2 | 8/2008 |

OTHER PUBLICATIONS

Anderson, 1946, Proc. Natl. Acad. Sci. USA 32:120-128.*
Johansson et al, Transcriptome analysis of a shikimic acid producing strain of *Escherichia coli* W3110 grown under carbon- and phosphate-limited conditions. J Biotechnol. Dec. 1, 2006;126(4):528-45. Epub May 17, 2006.*
Aitken et al., "The Enzymology of Cystathionine Biosynthesis: Strategies for the Control of Substrate and Reaction Specificity," Archives of Biochemistry and Biophysics, vol. 433, 2005, pp. 166-175.
Anderson; "Growth Requirements of Virus-Resistant Mutants of *Escherichia coli* Strain B," Department of Biology, Vanderbilt University, Proceedings of the National Academy of Sciences of USA, vol. 32, Communicated Mar. 21, 1946, pp. 120-128.
ATCC, Host cells ATCC# 27325; W311 0. downloaded Oct. 9, 2012.
Carrier et al., "Library of Synthetic 5' Secondary Structures to Manipulate mRNA Stability in *Escherichia coli*," Biotechnology Progress, vol. 15, No. 1, 1999 (Published on web: Jan. 9, 1999), pp. 58-64 (8 pages).
Datsenko et al., "One-Step Inactivation of Chromosomal Genes in *Escherichia coli* K-12 Using K-12 Using PCR Products," PNAS, vol. 97, No. 12, Jun. 6, 2000, pp. 6640-6645.
Figge, "Methionine Biosynthesis in *Escherichia coli* and Corynebacterium glutamicum," Microbiology Monographs vol. 5, V.F. Wendisch: Amino Acid Biosynthesis, Published Online: Dec. 9, 2006, pp. 164-194 (31 pages), XP008095720.
Gomes et al., "Production of L-Methionine by Submerged Fermentation: A Review," Enzyme and Microbial Technology, vol. 37, 2005, pp. 3-18, XP004873851.
International Search Report based on PCT/EP2008/062859 dated Apr. 23, 2010.
Johansson et al., "Transcriptome Analysis of a Shikimic Acid Producing Strain of *Escherichia coli* W3110 Grown under Carbon- and Phosphate-limited Conditions," Journal of Biotechnology, vol. 126, 2006, pp. 528-545, XP005720322.
Kröemer et al., "Accumulation of Homolanthionine and Activation of a Novel Pathway for Isoleucine Biosynthesis in Corynebacterium glutamicum McbR Deletion Strains," Journal of Bacteriology, vol. 188, No. 2, Jan. 2006, pp. 609-618.
Kröemer et al., "Metabolic Pathway Analysis for Rational Design of L-Methionine Production by *Escherichia coli* and Corynebacterium glutamicum," Metabolic Engineering, vol. 8, 2006 (Available online: Apr. 18, 2006), pp. 353-369, XP005502384.
Kumar et al., "Methionine Production by Fermentation," Biotechnology Advances vol. 23, 2005 (Available online: Oct. 12, 2004, pp. 41-61, XP004682516.
Liebl et al., "Requirement of Chelating Compounds for the Growth of Corynebacterium Glutamicum in Synthetic Media," Applied Microbiology and Biotechnology, 1989, vol. 32, pp. 205-210.

(Continued)

*Primary Examiner* — Sheridan Swope
(74) *Attorney, Agent, or Firm* — Birch, Stewart, Kolasch & Birch, LLP.

(57) ABSTRACT

Process for the production of methionine or its derivatives by culturing a microorganism in an appropriate culture medium comprising a source of carbon and a source of sulfur. The microorganism and/or the culture medium are modified in such way that the methionine/carbon source yield is increased. The isolation of methionine or its derivates from the fermentation medium is also described.

4 Claims, 2 Drawing Sheets

Figure 1:
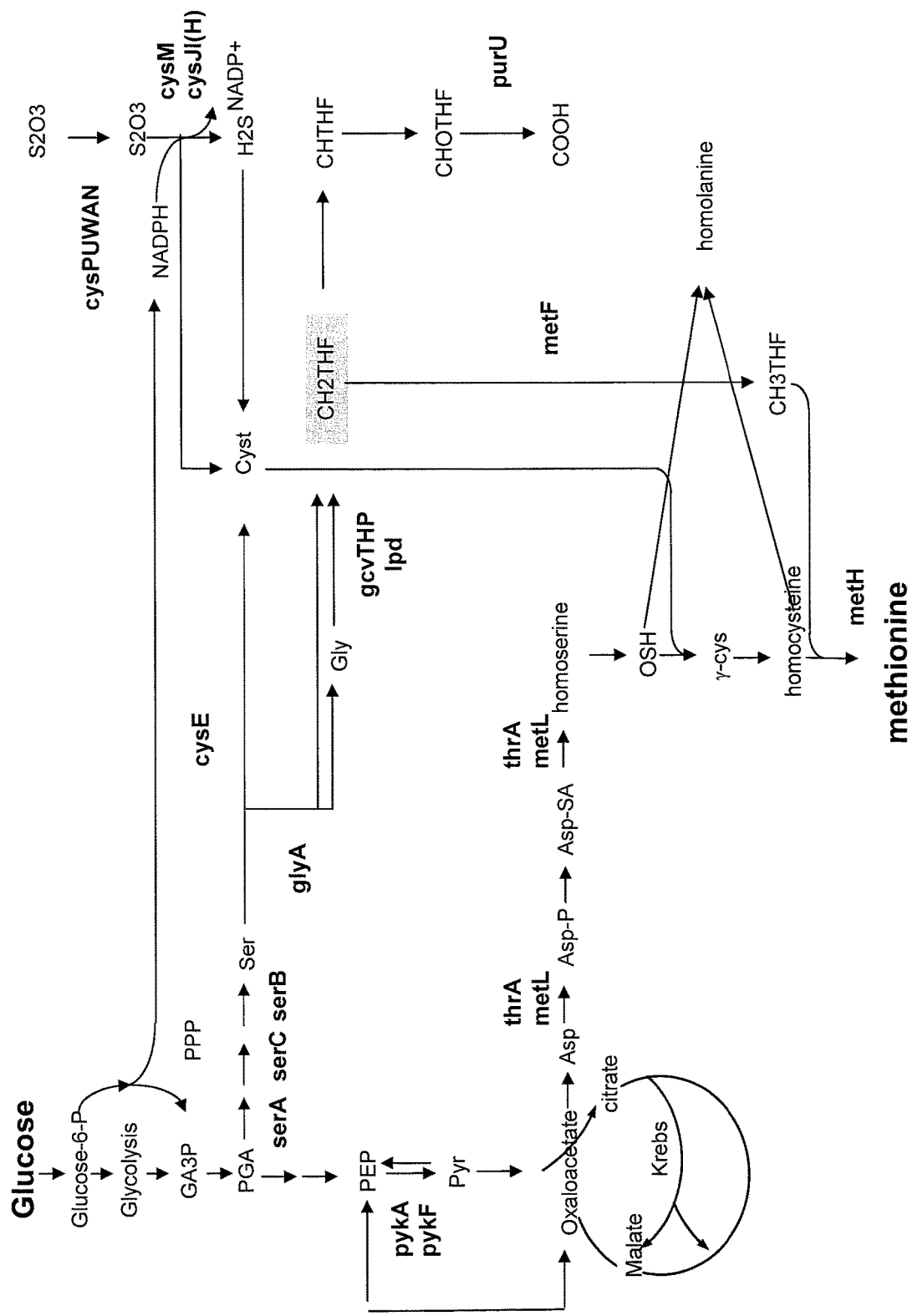

Specification includes a Sequence Listing.

(56) References Cited

OTHER PUBLICATIONS

Nagy et al., "purU, a Source of Formate for purT-Dependent Phosphoribosyl-N-Formylglycinamide Synthesis," Journal of Bacteriology, vol. 175, No. 21, Nov. 1993, pp. 7066-7073.

Riedel et al; "Characterization of the Phosphoenolpyruvate Carboxykinase Gene from Corynebacterium Glutamicum and Significance of the Enzyme for Growth and Amino Acid Protection," Journal of Molecular Microbiology and Biotechnology, vol. 3, No. 4, 2001, pp. 573-583.

Sauer et al., "The PEP-pyruvate-oxaloacetate Node as the Switch Point for Carbon Flux Distribution in Bacteria," FEMS Microbiology Reviews, vol. 29, 2005 (Published online: Nov. 28, 2004), pp. 765-794.

Saunderson, "Comparative Metabolism of L-Methionine, DL-Methionine and DI-2Hydroxy 4-Methylthiobutanoic Acid by Broiler Chicks," British Journal of Nutrition, vol. 54, 1985, pp. 621-633.

Schaefer et al., "Automated Sampling Device for Monitoring Intracellular Metabolite Dynamics," Analytical Biochemistry, vol. 270, 1999, pp. 88-96.

Trötschel et al, "Characterization of Methionine Export in Corynebacterium Glutamicum," Journal of Bacteriology, vol. 187, No. 11, Jun. 2005, pp. 3786-3794.

Tuite et al., "Homocysteine Toxicity in *Escherichia coli* is Caused by a Perturbation of Branched-Chain Amino Acid Biosynthesis," Journal of Bacteriology, vol. 187, No. 13, Jul. 2005; pp. 4362-4371.

Usuda et al, "Effects of Deregulation of Methionine Biosynthesis on Methionine Excretion in *Escherichia coli*," Applied and Environmental Microbiology, vol. 71, No. 6, Jun. 2005, p. 3228-3234.

Wendisch et al., "Metabolic Engineering of *Escherichia coli* and Corynebacterium glutamicum for Biotechnological Production of Organic Acids and Amino Acids," Current Opinion in Microbiology, vol. 9, 2006 (Available online: Apr. 17, 2006), pp. 268-274.

* cited by examiner

SEQUENCE LISTING

<160> NUMBER OF SEQ ID NOS: 38

<210> SEQ ID NO 1
<211> LENGTH: 128
<212> TYPE: DNA
<213> ORGANISM: Artificial
<220> FEATURE:
<223> OTHER INFORMATION: PRIMER

<400> SEQUENCE: 1
gcgcgagtga gttctttttc agtaagttaa cggccattgc gcacccttat aaatttaatg      60
actttcttcc acacattata cgagccggat gattaattgt caacagcttg taggctggag     120
ctgcttcg                                                              128

<210> SEQ ID NO 2
<211> LENGTH: 121
<212> TYPE: DNA
<213> ORGANISM: Artificial
<220> FEATURE:
<223> OTHER INFORMATION: PRIMER

<400> SEQUENCE: 2
ccaaatcacc aaacggtata taaaaccgtt actcctttca cgtccgttat aaatatgatg      60
gctattatca cactggctca ccttcgggtg ggcctttctg ccatatgaat atcctcctta     120
g                                                                     121

<210> SEQ ID NO 3
<211> LENGTH: 23
<212> TYPE: DNA
<213> ORGANISM: Artificial
<220> FEATURE:
<223> OTHER INFORMATION: PRIMER

<400> SEQUENCE: 3
gcaggatttg tacgtcggtc acc                                              23

<210> SEQ ID NO 4
<211> LENGTH: 24
<212> TYPE: DNA
<213> ORGANISM: Artificial
<220> FEATURE:
<223> OTHER INFORMATION: PRIMER

<400> SEQUENCE: 4
cgtcttgaac taagttcacc aggc                                             24

<210> SEQ ID NO 5
<211> LENGTH: 115
<212> TYPE: DNA
<213> ORGANISM: Artificial
<220> FEATURE:
<223> OTHER INFORMATION: PRIMER

<400> SEQUENCE: 5
ccagtaagca aagctgtttc tgcgccctgt cagcgcccat aaaacagaag agattccaca      60
cattatacga gccggatgat taattgtcaa cagcttgtag gctggagctg cttcg          115

<210> SEQ ID NO 6
<211> LENGTH: 114
<212> TYPE: DNA
<213> ORGANISM: Artificial
<220> FEATURE:
<223> OTHER INFORMATION: PRIMER

<400> SEQUENCE: 6

```
ggttattagt tatcgctatc ccgtctttaa tccacaccgt ttgccccgtt aaccttacct        60
tcacactggc tcaccttcgg gtgggccttt ctgccatatg aatatcctcc ttag            114
```

<210> SEQ ID NO 7
<211> LENGTH: 23
<212> TYPE: DNA
<213> ORGANISM: Artificial
<220> FEATURE:
<223> OTHER INFORMATION: PRIMER

<400> SEQUENCE: 7

```
gcagttcgac aagttctttc acc                                              23
```

<210> SEQ ID NO 8
<211> LENGTH: 26
<212> TYPE: DNA
<213> ORGANISM: Artificial
<220> FEATURE:
<223> OTHER INFORMATION: PRIMER

<400> SEQUENCE: 8

```
ccagaacaca cacccctaac atagcg                                           26
```

<210> SEQ ID NO 9
<211> LENGTH: 135
<212> TYPE: DNA
<213> ORGANISM: Artificial
<220> FEATURE:
<223> OTHER INFORMATION: PRIMER

<400> SEQUENCE: 9

```
ccaccatgcg agcgccgcaa agcgtgtgtt gttcgtacaa aggagtctgt tgtgccataa      60
tatacctcct tattccacac attatacgag ccggatgatt aattgtcaac agctctgtag     120
gctggagctg cttcg                                                      135
```

<210> SEQ ID NO 10
<211> LENGTH: 78
<212> TYPE: DNA
<213> ORGANISM: Artificial
<220> FEATURE:
<223> OTHER INFORMATION: PRIMER

<400> SEQUENCE: 10

```
ctgtcgcgat ttttgcattt tttaaccata agctaatgtg atgatcaatt ttaccttaca      60
tatgaatatc ctccttag                                                    78
```

<210> SEQ ID NO 11
<211> LENGTH: 23
<212> TYPE: DNA
<213> ORGANISM: Artificial
<220> FEATURE:
<223> OTHER INFORMATION: PRIMER

<400> SEQUENCE: 11

```
ctatcacacc gccagaggca ttc                                              23
```

<210> SEQ ID NO 12
<211> LENGTH: 22
<212> TYPE: DNA
<213> ORGANISM: Artificial
<220> FEATURE:
```

<223> OTHER INFORMATION: PRIMER

<400> SEQUENCE: 12
cccatcacac tttcatctcc cg					22

<210> SEQ ID NO 13
<211> LENGTH: 101
<212> TYPE: DNA
<213> ORGANISM: Artificial
<220> FEATURE:
<223> OTHER INFORMATION: PRIMER

<400> SEQUENCE: 13
cgcggcgggt gccaacgttg tacgtatgaa cttttctcac ggctcgcctg aagatcacaa			60 aatgcgcgcg gataaagttc gtgtaggctg gagctgcttc g					101

<210> SEQ ID NO 14
<211> LENGTH: 101
<212> TYPE: DNA
<213> ORGANISM: Artificial
<220> FEATURE:
<223> OTHER INFORMATION: PRIMER

<400> SEQUENCE: 14
cgccgcatcc ggcaacgtac ttactctacc gttaaaatac gcgtggtatt agtagaaccc			60 acggtactca tcacgtcgcc ccatatgaat atcctcctta g					101

<210> SEQ ID NO 15
<211> LENGTH: 23
<212> TYPE: DNA
<213> ORGANISM: Artificial
<220> FEATURE:
<223> OTHER INFORMATION: PRIMER

<400> SEQUENCE: 15
ggcaattacc ctcgacgtac cgg					23

<210> SEQ ID NO 16
<211> LENGTH: 25
<212> TYPE: DNA
<213> ORGANISM: Artificial
<220> FEATURE:
<223> OTHER INFORMATION: PRIMER

<400> SEQUENCE: 16
ccgcctctaa cagatcatcc atcgg					25

<210> SEQ ID NO 17
<211> LENGTH: 98
<212> TYPE: DNA
<213> ORGANISM: Artificial
<220> FEATURE:
<223> OTHER INFORMATION: PRIMER

<400> SEQUENCE: 17
cccatccttc tcaacttaaa gactaagact gtcatgaaaa agaccaaaat tgtttgcacc			60 atcggaccga aaccgaatg taggctggag ctgcttcg					98

<210> SEQ ID NO 18
<211> LENGTH: 99
<212> TYPE: DNA
<213> ORGANISM: Artificial
<220> FEATURE:
<223> OTHER INFORMATION: PRIMER

<400> SEQUENCE: 18

```
ggacgtgaac agatgcggtg ttagtagtgc cgctcggtac cagtgcacca gaaaccataa    60
ctacaacgtc acctttgtgc atatgaatat cctccttag                           99
```

<210> SEQ ID NO 19
<211> LENGTH: 22
<212> TYPE: DNA
<213> ORGANISM: Artificial
<220> FEATURE:
<223> OTHER INFORMATION: PRIMER

<400> SEQUENCE: 19

```
gcgtaacctt ttccctggaa cg                                             22
```

<210> SEQ ID NO 20
<211> LENGTH: 24
<212> TYPE: DNA
<213> ORGANISM: Artificial
<220> FEATURE:
<223> OTHER INFORMATION: PRIMER

<400> SEQUENCE: 20

```
gcgttgctgg agcaacctgc cagc                                           24
```

<210> SEQ ID NO 21
<211> LENGTH: 101
<212> TYPE: DNA
<213> ORGANISM: Artificial
<220> FEATURE:
<223> OTHER INFORMATION: PRIMER

<400> SEQUENCE: 21

```
ggtaaaaaat ttaaaaagtg ctgcggccaa taatggttga cggtacggtt tagcaaacac    60
tctcaacaag gttttccag ctgtaggctg gagctgcttc g                         101
```

<210> SEQ ID NO 22
<211> LENGTH: 101
<212> TYPE: DNA
<213> ORGANISM: Artificial
<220> FEATURE:
<223> OTHER INFORMATION: PRIMER

<400> SEQUENCE: 22

```
ggttgcgtaa ttttcatccg taacggatta aaggtaacca gttatttttg ctggcgatta    60
aagaataatc gttcgattac ccatatgaat atcctcctta g                        101
```

<210> SEQ ID NO 23
<211> LENGTH: 24
<212> TYPE: DNA
<213> ORGANISM: Artificial
<220> FEATURE:
<223> OTHER INFORMATION: PRIMER

<400> SEQUENCE: 23

```
ggaatgcaat cgtagccaca tcgc                                           24
```

<210> SEQ ID NO 24
<211> LENGTH: 24
<212> TYPE: DNA
<213> ORGANISM: Artificial
<220> FEATURE:
<223> OTHER INFORMATION: PRIMER
```

<400> SEQUENCE: 24
gcggattcgt tgggaagttc aggg    24

<210> SEQ ID NO 25
<211> LENGTH: 35
<212> TYPE: DNA
<213> ORGANISM: Artificial
<220> FEATURE:
<223> OTHER INFORMATION: PRIMER

<400> SEQUENCE: 25
tgctctagag tccgcgctgt gcaaatccag aatgg    35

<210> SEQ ID NO 26
<211> LENGTH: 34
<212> TYPE: DNA
<213> ORGANISM: Artificial
<220> FEATURE:
<223> OTHER INFORMATION: PRIMER

<400> SEQUENCE: 26
cccaagctta actctctaca acagaaataa aaac    34

<210> SEQ ID NO 27
<211> LENGTH: 31
<212> TYPE: DNA
<213> ORGANISM: Artificial
<220> FEATURE:
<223> OTHER INFORMATION: PRIMER

<400> SEQUENCE: 27
ctagtctaga ttagtacagc agacgggcgc g    31

<210> SEQ ID NO 28
<211> LENGTH: 35
<212> TYPE: DNA
<213> ORGANISM: Artificial
<220> FEATURE:
<223> OTHER INFORMATION: PRIMER

<400> SEQUENCE: 28
tcccccggga agcttccgtc agggcgtggt gaccg    35

<210> SEQ ID NO 29
<211> LENGTH: 32
<212> TYPE: DNA
<213> ORGANISM: Artificial
<220> FEATURE:
<223> OTHER INFORMATION: PRIMER

<400> SEQUENCE: 29
atgcgcatgc ccacccttttg aaaatttgag ac    32

<210> SEQ ID NO 30
<211> LENGTH: 73
<212> TYPE: DNA
<213> ORGANISM: Artificial
<220> FEATURE:
<223> OTHER INFORMATION: PRIMER

<400> SEQUENCE: 30
gcatgtcgac atcccggggc agaaaggccc acccgaaggt gagccagtgt gattacttct    60
gattcaggct gcc    73

```
<210> SEQ ID NO 31
<211> LENGTH: 39
<212> TYPE: DNA
<213> ORGANISM: Artificial
<220> FEATURE:
<223> OTHER INFORMATION: PRIMER

<400> SEQUENCE: 31
tcatcggatc catcaagctt gaaagaatgt gatgaagtg                              39

<210> SEQ ID NO 32
<211> LENGTH: 45
<212> TYPE: DNA
<213> ORGANISM: Artificial
<220> FEATURE:
<223> OTHER INFORMATION: PRIMER

<400> SEQUENCE: 32
atctagtaag cttagtgaat cgttacgac agatttgatg gcgcg                        45

<210> SEQ ID NO 33
<211> LENGTH: 39
<212> TYPE: DNA
<213> ORGANISM: Artificial
<220> FEATURE:
<223> OTHER INFORMATION: PRIMER

<400> SEQUENCE: 33
atgcgctaaa gcttggttat tagcgaatag acaaatcgg                              39

<210> SEQ ID NO 34
<211> LENGTH: 39
<212> TYPE: DNA
<213> ORGANISM: Artificial
<220> FEATURE:
<223> OTHER INFORMATION: PRIMER

<400> SEQUENCE: 34
gcatgatcga attctgcaga cgtaaaaaaa gcggcgtgg                              39

<210> SEQ ID NO 35
<211> LENGTH: 115
<212> TYPE: DNA
<213> ORGANISM: Artificial
<220> FEATURE:
<223> OTHER INFORMATION: PRIMER

<400> SEQUENCE: 35
ggctctgatt cagggcatcc cgctggctgg cgtgaaaaaa gctcataata tacctcctcg       60
tcaacaatat ctcactcgag ataactccac ctattccaca cattatacga gccgg           115

<210> SEQ ID NO 36
<211> LENGTH: 136
<212> TYPE: DNA
<213> ORGANISM: Artificial
<220> FEATURE:
<223> OTHER INFORMATION: PRIMER

<400> SEQUENCE: 36
ccttcatctt tacatctgga cgtctaaacg gatagatgtg cacaacacaa catataacta      60
caagcgattg atgaggtaag gttcacactg gctcaccttc gggtgggcct ttctgccata     120
tgaatatcct ccttag                                                     136

<210> SEQ ID NO 37
```

```
<211> LENGTH: 29
<212> TYPE: DNA
<213> ORGANISM: Artificial
<220> FEATURE:
<223> OTHER INFORMATION: PRIMER

<400> SEQUENCE: 37
gcccggtact catgttttcg ggtttatgg                                          29

<210> SEQ ID NO 38
<211> LENGTH: 28
<212> TYPE: DNA
<213> ORGANISM: Artificial
<220> FEATURE:
<223> OTHER INFORMATION: PRIMER

<400> SEQUENCE: 38
ccgttattcc agtagtcgcg tgcaatgg                                           28
```

INCREASING METHIONINE YIELD

This application is a Continuation of copending application Ser. No. 12/681,177, filed on Apr. 1, 2010, which was filed as PCT International Application No. PCT/EP2008/062859 on Sep. 25, 2008, which claims the benefit under 35 U.S.C. § 119(a) to PCT International Application No. PCT/EP2007/060433 on Oct. 2, 2007, all of which are hereby expressly incorporated by reference into the present application.

FIELD OF THE INVENTION

The present invention relates to a process for the production of methionine or its derivatives by culturing a microorganism in an appropriate culture medium comprising a source of carbon and a source of sulfur. The microorganism and/or the culture medium were modified in a way that the methionine/carbon source yield is increased. The isolation of methionine or its derivates from the fermentation medium is also claimed.

PRIOR ART

Sulphur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Nevertheless most of the methionine which is produced is added to animal feed.

With the decreased use of animal-derived proteins as a result of BSE and chicken flu, the demand for pure methionine has increased. Chemically D,L-methionine is commonly produced from acrolein, methyl mercaptan and hydrogen cyanide. Nevertheless the racemic mixture does not perform as well as pure L-methionine, as for example in chicken feed additives (Saunderson, C. L., (1985) British Journal of Nutrition 54, 621-633). Pure L-methionine can be produced from racemic methionine e.g. through the acylase treatment of N-acetyl-D,L-methionine which increases production costs dramatically. The increasing demand for pure L-methionine coupled to environmental concerns render microbial production of methionine attractive.

Microorganisms have developed highly complex regulatory mechanisms that fine-tune the biosynthesis of cell components thus permitting maximum growth rates. Consequently only the required amounts of metabolites, such as amino acids, are synthesized and can usually not be detected in the culture supernatant of wild-type strains. Bacteria control amino acid biosynthesis mainly by feedback inhibition of enzymes, and repression or activation of gene transcription. Effectors for these regulatory pathways are in most cases the end products of the relevant pathways. Consequently, strategies for overproducing amino acids in microorganisms require the deregulation of these control mechanisms.

The pathway for L-methionine synthesis is well known in many microorganisms (FIG. 1). Methionine is derived from the amino acid aspartate, but its synthesis requires the convergence of two additional pathways, cysteine biosynthesis and C1 metabolism.

Aspartate is synthesized from oxaloacetate. In E. coli a stable oxaloacetate pool is required for the proper functioning of the citric acid cycle. Therefore the transformation of oxaloacetate into aspartate requires reactions that compensate for oxaloacetate withdrawal from this pool. Several pathways, called anaplerotic reactions, fulfill these functions in E. coli (Sauer & Eikmanns (2005) FEMS Microbiol Reviews 29 p 765-94). Under exponential growth conditions and glucose excess, PEP carboxylase catalyzes the carboxylation of PEP yielding oxaloacetate. Carboxylation efficiency depends among other on the intracellular PEP concentration. PEP is a central metabolite that undergoes a multitude of reactions. One of them, glycolytic transformation of PEP to pyruvate is not essential for E. coli, since the import of glucose via the PTS system transforms one of two PEP molecules generated from glucose into pyruvate. In glycolysis the enzyme pyruvate kinase, which in E. coli is encoded by two isoenzymes encoded by the genes pykA and pykF, catalyzes the transformation of PEP to pyruvate.

Aspartate is converted into homoserine by a sequence of three reactions. Homoserine can subsequently enter the threonine/isoleucine or methionine biosynthetic pathway. In E. coli entry into the methionine pathway requires the acylation of homoserine to succinyl-homoserine. This activation step allows subsequent condensation with cysteine, leading to the thioether-containing cystathionine, which is hydrolyzed to give homocysteine. The final methyl transfer leading to methionine is carried out by either a $B_{12}$-dependent or a $B_{12}$-independent methyltransferase.

Methionine biosynthesis in E. coli is regulated by repression and activation of methionine biosynthetic genes via the MetJ and MetR proteins, respectively (reviewed in Figge R M (2006), ed Wendisch V F, Microbiol Monogr (5) Amino acid biosynthesis p 164-185). MetJ together with its corepressor S-adenosylmethionine is known to regulate the genes metA, metB, metC, metE and metF. Other genes encoding enzymes involved in methionine production, such as glyA, metE, metH and metF are activated by MetR in presence of its co-activator homocysteine, whereas metA is only activated by MetR in the absence of homocysteine. All these enzymes are involved in the production and the transfer of C1 units from serine to methionine. GlyA encoding serine hydroxymethyltransferase catalyzes the conversion of serine to glycine and the concomitant transfer of a C1 unit on the coenzyme tetrahydrofolate (THF). Glycine can then be transformed into $CO_2$, $NH_3$ while another C1 unit is transferred onto THF. This reaction is catalyzed by the glycine cleavage complex encoded by the genes gcvTHP and lpd.

C1 units produced by the two reactions in form of methylene-THF can subsequently either be reduced to methyl-THF or further oxidized to formyl-THF. Methionine biosynthesis requires the reduction to methyl-THF. Thus the oxidation reaction competes with methionine biosynthesis for C1 units. Formyl-THF or formate is required for the biosynthesis of purines and histidine. In E. coli formyl-THF can be transformed into THF and free formate in a reaction catalyzed by formyl-THF deformylase encoded by the purU gene (Nagy et al. (1995) J. Bacteriol 177 (5) p. 1292-98). The reduction of methylene-THF to methyl-THF is catalyzed by the MetF protein. Transfer of the methyl group onto homocysteine is either catalyzed by MetH via vitamin B12 or directly by MetE. The MetH enzyme is known to have a catalytic rate that is hundred times higher than the MetE enzyme. In the absence of vitamin $B_{12}$ and thus active MetH, MetE can compose up to 5% of the total cellular protein. The presence of active MetH reduces MetE activity probably by reducing the amount of homocysteine that normally activates the transcription of metE via MetR. Therefore the production of methionine via MetH saves important resources for the cell, since MetE is not expressed in large quantities. The accumulation of homocysteine is toxic for *E. coli* (Tuite et al., 2005 J. Bacteriol, 187, 13, 4362-4371.) and at the same time has a negative, regulatory effect on metA expression via MetR. Thus a strong expression of the enzymes MetH and/or MetE is clearly required for efficient methionine production.

In *E. coli* reduced sulfur is integrated into cysteine and then transferred onto the methionine precursor 0-succinyl-homoserine, a process called transulfuration (reviewed in Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. *Escherichia coli* and *Salmonella*: Cellular and Molecular Biology. American Society for Microbiology). Cysteine is produced from O-acetylserine and $H_2S$ by sulfhydrylation. The process is negatively feed-back regulated by the product, cysteine, acting on serine transacetylase, encoded by cysE. N-acetyl-serine, which is spontaneously produced from O-acetyl-serine, together with the transcription factor CysB activates genes encoding enzymes involved in the transport of sulfur compounds, their reduction to $H_2S$ and their integration in the organo-sulfur compound cysteine, which, as methionine, is an essential amino acid.

In the absence of cysteine, MetB catalyzes the conversion of the methionine-precursor O-succinyl homoserine into ammonia, α-ketobutyrate and succinate, a reaction called γ-elimination (Aitken & Kirsch, 2005, Arch Biochem Biophys 433, 166-75). α-ketobutyrate can subsequently be converted into isoleucine. This side reaction is not desirable for the industrial production of methionine, since the two amino acids are difficult to separate. Thus low γ-elimination activity or other means to keep isoleucine production low are important aspects for the industrial production of methionine. The provisional patent application U.S. 60/650,124 describes how γ-elimination can be reduced by optimizing the enzyme MetB. Optimizing cysteine biosynthesis can also reduce γ-elimination and thus the production of the byproduct isoleucine and constitutes an embodiment of this invention.

General Disclosure of the Invention

The invention relates to a method for the production of methionine, its derivatives, or precursors in a fermentative process comprising the following steps:
culturing a modified microorganism in an appropriate culture medium comprising a source of carbon and a source of sulfur, and
recovering methionine from the culture medium,
wherein compared to a non-modified microorganism or method the microorganism or the method has been modified to present an enhanced methionine/carbon source yield by at least one of the following modifications and combinations thereof:
1—A decrease in the deformylation of formyl-THF in the microorganism
2—A decrease of the consumption of phosphoenol pyruvate (PEP) in the microorganism
3—A limitation of the growth of the microorganism by limiting or starving the microorganism for one or several inorganic substrates in the culture medium.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms. Genes and proteins from other organisms may also be specified, particularly for *Corynebacterium glutamicum* as additional information. The purpose of this additional information is not to limit the general definition for a gene or a protein.

In a specific embodiment of the invention methionine/carbon source yield is increased by decreasing the deformylation of formyl-THF, which is accomplished by attenuating the expression of the purU gene (YP_001137322 in *C. glutamicum*). The PurU enzyme catalyzes the formyl-THF deformylase reaction. The attenuation of the deformylase activity increases the production of methyl-THF that is required for methylation of homocysteine. Loss of C1 metabolites by deformylation leads to an increased production of homocysteine that cannot be transformed into methionine. Homocysteine can then be a substrate for the enzyme cystathionine gamma synthase (MetB) that can catalyze the reaction between O-succinylhomoserine and homocysteine resulting in the production of homolanthionine.

In another specific embodiment of the invention the methionine/carbon source yield is increased by decreasing the consumption of phosphoenol pyruvate (PEP), which is accomplished by the attenuation of at least one or both of the pyruvate kinase encoding genes pykA and pykF. Increased availability of PEP can increase the production of oxaloacetate an important precursor of aspartate, which in turn is a precursor of methionine. *C. glutamicum* harbors only one pyruvate kinase gene which corresponds to YP_226326.

In another embodiment of the invention methionine/carbon source yield is increased by limiting the growth of the microorganism or starving the microorganism for an inorganic substrate. This might be achieved by limiting the amount of available phosphate and/or potassium in the culture medium. Such a limitation of the cell growth allows the improvement of the methionine/carbon source yield, since carbon is not used for the production of biomass and/or the maintenance of this biomass, but for the production of methionine. In particular, the concentration of phosphate in the culture medium permits growth to an $OD_{600}$ of less than 200, preferentially of 150, more preferentially of 100. An $OD_{600}$ of 100 corresponds to 30 to 35 g/l biomass for *E. coli*, for yeast to 40-50 g/l. For other microorganisms the conversion factor will be known by the expert in the field. For *E. coli* the amount of phosphate required to produce one g biomass is between 10 and 20 mg, preferentially about 18 mg. The amount of potassium required to produce one g biomass is between 10 and 20 mg, preferentially about 18 mg. For *Corynebacterium glutamicum* the amount of phosphate required to produce one g biomass is between 14 and 21 mg, preferentially about 17 mg. The amount of potassium required to produce one g biomass is between 23 and 33 g, preferentially about 28 mg. For other microorganisms the conversion factor will be known by the expert in the field.

The microorganism is grown in rich or minimal medium, preferentially in minimal medium. Suitable minimal media are described below.

These three means to modulate the methionine/carbon source yield can be used alone or combined with one or two of the other means.

Accordingly, the reduction of the formyl-THF deformylation by attenuating the expression of the purU gene can be associated with a reduction of the consumption of PEP by attenuating the expression of the genes pykA, pykF or both and with a limitation or starvation of phosphate and/or potassium in the culture medium.

Similarly, the reduction of the formyl-THF deformylation by attenuating the expression of the purU gene can be associated with a reduction of the consumption of PEP by attenuating the expression of the genes pykA, pykF or both.

Similarly, the reduction of the formyl-THF deformylation by attenuating the expression of the purU gene can be associated with a limitation or starvation of phosphate and/or potassium in the culture medium.

Similarly, the reduction of the consumption of PEP by attenuating the expression of the genes pykA, pykF or both can be associated with a limitation or starvation of phosphate and/or potassium in the culture medium.

As used herein the following terms may be used for the interpretation of the claims and specifications.

According to the invention the terms 'culture', 'fermentation" or "fermentative process' are used interchangeably to denote the growth of bacteria on an appropriate growth medium containing a simple carbon source.

Total methionine/carbon source yield is defined as the amount of methionine+NAM (for NAM mass of equivalent amount of methionine) (g) %/per glucose (g) consumed during the fermentation run.

Derivatives of methionine originate from methionine transforming and/or degrading pathways. In particular these products are S-adenosyl-methionine (SAM) thio-methyl-ribose and N-acetylmethionine (NAM). Especially NAM is an easily recoverable methionine derivative that may be isolated and transformed into methionine by deacylation. The phrase "recovering methionine from the culture medium" designates the action of recovering methionine, SAM and NAM and all other derivatives that may be useful.

Precursors of methionine are defined as metabolites that are part of the methionine specific metabolic pathway or can be derived of these metabolites. In particular precursors are O-succinyl-homoserine (OSH), gamma-cystathionine, homocysteine and homolanthionine. The methionine specific pathway starts with the transformation of homoserine to succinylhomoserine by the enzyme homoserine succinyl transferase (MetA).

The term "microorganism" designates a bacterium, yeast or a fungus. Preferentially, the microorganism is selected among Enterobacteriaceae, Bacillaceae, Streptomycetaceae and Corynebacteriaceae. More preferentially the microorganism is a species of *Escherichia, Klebsiella, Pantoea, Salmonella* or *Corynebacterium*. Even more preferentially the microorganism is either the species *Escherichia coli* or *Corynebacterium glutamicum*.

The term "modified microorganism" denotes a microorganism that has been genetically modified with the goal to increase the methionine/carbon source yield. The man skilled in the art knows how to modulate the expression of specific genes. Usual modifications include transforming microorganisms with genetic elements, including gene replacements, modification of promoters, and introduction of vectors for the expression of heterologous genes.

The term "methionine/carbon source yield" defines the quantity of methionine obtained during the fermentation divided by the quantity of the carbon source that has been consumed. It can be expressed in percent g methionine/g carbon source or mol methionine/mol carbon source. The term "enhanced" in this context describes a measurable increase compared to the microorganism without the specified modifications and/or the culture medium without the modifications. In preferred embodiments, the increase is of at least 2% g/g, preferably of at least 4% g/g, more preferably of at least 7% g/g. The total methionine/carbon source yield is preferentially at least 7% g/g, preferentially at least 12% g/g, preferentially at least 15% g/g, most preferentially at least 19% g/g.

To measure this increase the amount of consumed glucose and produced methionine has to be determined. The quantity of the carbon source that has been consumed is calculated by determining the glucose concentration in the growth medium by HPLC with refractometric detection or according to the method of Brix for fed-batch solutions. For batch cultures the consumed glucose corresponds to the amount of residual glucose at the beginning of the experiment from which the amount of the residual glucose at the end of the experiment is subtracted. For fed batch fermentation (see examples for a detailed explanation) the amount of consumed glucose corresponds to the sum of glucose in the batch culture, the added glucose in the inoculum and the amount of glucose injected during the fed batch phase from which the amount of residual glucose at the end of the experiment is subtracted.

The term "methionine obtained" includes L-methionine and the easily recoverable methionine derivative NAM. The quantity of methionine obtained in the medium is measured by HPLC after OPA/Fmoc derivatization with fluorometric detection using L-methionine (Fluka, Ref 64319) as a standard. The amount of NAM is determined using refractometric HPLC using NAM (Sigma, Ref 01310) as a standard.

The term 'carbon source' according to the present invention denotes any source of carbon that can be used by those skilled in the art to support the normal growth of a microorganism, which can be hexoses (such as glucose, galactose or lactose), pentoses, monosaccharides, disaccharides, oligosaccharides (such as sucrose, cellobiose or maltose), molasses, starch or its derivatives, hemicelluloses, glycerol and combinations thereof. An especially preferred simple carbon source is glucose. Another preferred simple carbon source is sucrose.

The term 'attenuation of the expression of a gene' according to the invention denotes the partial or complete suppression of the expression of a gene, which is then said to be 'attenuated'. This suppression of expression can be either an inhibition of the expression of the gene, a deletion of all or part of the promoter region necessary for the gene expression, a deletion in the coding region of the gene, or the exchange of the wildtype promoter by a weaker natural or synthetic promoter. Preferentially, the attenuation of a gene is essentially the complete deletion of that gene, which can be replaced by a selection marker gene that facilitates the identification, isolation and purification of the strains according to the invention. A gene is inactivated preferentially by the technique of homologous recombination (Datsenko, K. A. & Wanner, B. L. (2000) "One-step inactivation of chromosomal genes in *Escherichia coli* K-12 using PCR products". Proc. Natl. Acad. Sci. USA 97: 6640-6645).

The terms "enhanced" or "overexpressed" in this context describe the increase in the intracellular activity of an enzymatic activity which is encoded by the corresponding DNA, for example by increasing the number of copies of the gene, using a stronger promoter or using an allele with increased activity and possibly combining these measures.

The terms "increased expression" "enhanced expression" or "overexpression" are used interchangeably in the text and have similar meaning.

To increase the expression of a gene it may be encoded chromosomally or extrachromosomally. Chromosomally there may be one or several copies on the genome that can be introduced by methods of recombination known to the expert in the field. Extrachromosomally genes may be carried by different types of plasmids that differ with respect to their origin of replication and thus their copy number in the cell. They may be present as 1-5 copies, about 20 or up to 500 copies, corresponding to low copy number plasmids with tight replication (pSC101, RK2), low copy number plasmids (pACYC, pRSF1010) or high copy number plasmids (pSK bluescript II)

In a preferred embodiment of the invention the gene may be expressed using promoters with different strength, which may be inducible. These promoters may be homologous or heterologous. The man skilled in the art knows which promoters are the most convenient, for example promoters Ptrc, Ptac, Plac or the lambda promoter cI are widely used.

Expression of the enzymes may be boosted or reduced by elements stabilizing or destabilizing the corresponding messenger RNA (Carrier and Keasling (1998) Biotechnol. Prog. 15, 58-64) or the proteins (e.g. GST tags, Amersham Biosciences) The present invention also relates to microorganisms that contain one or several alleles of the gene to be enhanced according to the invention.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models), that can be used on the Wellcome Trust Sanger Institute website, represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins), that can be used on the National Center for Biotechnology Information website, are obtained by comparing protein sequences from 66 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used from the National Center for Biotechnology Information website with the default parameters indicated on that website. The sequences obtained can then be exploited (e.g., aligned) using, for example, the programs CLUSTALW, that can be used on the European Bioinformatics Institute website, or MULTALIN, that can be used on the MultAlin website, with the default parameters indicated on those websites.

Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold Spring Harbor Lab., Cold Spring Harbor, N.Y.).

"Subjecting an organism to a limitation of an inorganic substrate" defines a condition under which growth of the microorganisms is governed by the quantity of a non-organic chemical supplied that still permits weak growth. Examples for these substrates are phosphate, potassium, magnesium or a combination of these.

Starving a microorganism for an inorganic substrate defines the condition under which growth of the microorganism stops completely due to the absence of the inorganic substrate. Examples for these substrates are phosphate, potassium, magnesium or a combination of these.

In this invention the inventors have aimed at increasing the methionine/carbon source yield by metabolic engineering of the production strain. In a particular embodiment of the invention, methionine/glucose and/or methionine/sucrose yield (g/g) is at least 10% g/g, preferentially at least 15% g/g, more preferentially 19% g/g.

In a specific embodiment of the invention, the expression of at least one gene involved in sulfur assimilation, the production of serine, its transformation to glycine or the cleavage of glycine is increased. It is advantageous to increase the sulfur assimilation of the microorganism since methionine is an amino acid containing sulfur ($C_5H_{11}NO_2S$). Moreover it is advantageous to increase the production of the amino acids serine and glycine and cleavage (i.e. the catabolism) of glycine. Glycine cleavage and transformation of serine to glycine are the two major reactions that produce methylene-THF that can be reduced to methyl-THF, which in turn is required for the methylation of homocysteine to methionine. Serine production is catalyzed by the enzymes 3-phosphoglycerate dehydrogenase, phosphoserine phosphatase and phosphoserine aminotransferase Glycine cleavage is catalyzed by the glycine cleavage complex.

In *E. coli* and *Corynebacterium glutamicum*, enzymes that could be increased in their activity and that are involved in the previously described activities are encoded by the following genes (followed by accession numbers and function of the corresponding polypeptide):

| gene | E. coli | accession number C. glutamicum (jekeium indicated in parentheses) | function |
|---|---|---|---|
| cysA | 1788761 | Cgl0216 | sulfate permease |
| cysU, cysT | 1788764 | Cgl0213 | component of sulfate ABC transporter |
| cysW | 1788762 | | membrane bound sulphate transport protein |
| cysH | 1789121 | Cgl2816 | adenylylsulfate reductase |
| cysI | 1789122 | Cgl2817 | sulfite reductase, alpha subunit |
| cysJ | 1789123 | YP_22705 | sulfite reductase, beta subunit |
| cysK | 1788754 | Cgl2562 | cysteine synthase |
| cysM | 2367138 | Cgl2136 | O-acetyl serine sulfhydrylase |
| cysP | 1788765 | | Periplasmic sulfate binding protein |
| cysE | 1790035 | Cgl2563 | Serine acetyltransferase |
| gcvT | 1789272 | (YP_249980) | Tetrahydrofolate dependent aminomethyl transferase |
| gcvH | 1789271 | (YP_249981) | Glycine cleavage, carrier of aminomethyl group |
| gcvP | 1789269 | (YP_249979) | Glycine dehydrogenase (decarboxylating) |
| lpd | 1786307 | YP_224666 | Lipoamide dehydrogenase |
| serA | 1789279 | YP_225572 | phosphoglycerate dehydrogenase, |

-continued

| gene | E. coli | C. glutamicum (jekeium indicated in parentheses) | function |
|---|---|---|---|
| serB | 1790849 | YP_226764 | phosphoserine phosphatase |
| serC | 1787136 | YP_225120 | phosphoserine aminotransferase |
| glyA | 1788902 | NP_60022 | serine hydroxymethyltransferase |

In a specific embodiment of the invention the expression of the operons cysPUWAM, encoding the sulfate/thiosulfate importer and thiosulfate specific cysteine synthase, and/or the operon cysJIH encoding sulfite reductase and PAPS reductase are increased. In case of Corynebacterium cysA, cysT, cyI and cysJ are preferably increased in their expression.

In another specific embodiment of the invention the expression of the operon gcvTHP, and/or gene lpd encoding the glycine cleavage complex is/are increased. The glycine cleavage complex may be introduced and overexpressed in Corynebacterium glutamicum by introducing the genes gcvTHP from Corynebacterium jekeium possibly as synthetic gene.

In another specific embodiment of the invention at least one gene involved in the in the production of glycine such as serA, serB, serC or glyA, is overexpressed.

In another embodiment of the invention, enzymes involved in the metabolic pathway of methionine biosynthesis may be overexpressed or their activity increased, to boost methionine production. In particular at least one of the following genes encoding for such enzymes may be overexpressed:

metF 1790377 Cg12171 5,10-Methylenetetrahydrofolate reductase metA (1790443) alleles encoding homoserine succinyltransferases with reduced feed-back sensitivity to S-adenosylmethionine and/or methionine as described in WO 2005/10856 or in the case of Corynebacterium glutamicum the gene metX Cg10652.

thrA or thrA (1786183) alleles encoding aspartokinases/homoserine dehydrogenases with reduced feed-back inhibition to threonine In the case of Corynebacterium glutamicum asp and hom, potentially feed-back resistant, as described in WO 2007/012078, may be overexpressed metH 1790450 Cg11507 B12-dependent homocysteine-N5-methyltetrahydrofolate transmethylase CysE 1790035 Cg12563 serine acetyltransferase The overexpression of metY (Cg10653) in C. glutamicum can be envisioned with or without overexpressing the genes aecD/metB. (Cg12309/Cg12446).

The overexpression of metF and metH has been suggested in WO 2007/077041 and WO2007/012078, which are incorporated by reference into this application. In this document the inventors have demonstrated that even further overexpression of metF using elements that stabilize the messenger RNA of metF further increased methionine production. These stabilizing elements are usually loop structures that reduce the attack by RNA degrading nucleases (Carrier and Keasling (1998) Biotechnol. Prog. 15, 58-64).

Overexpressing homoserine succinyltransferase alleles with reduced feed-back sensitivity to its inhibitors SAM and methionine is described in patent application WO 2005/111202 that is incorporated by reference into this application.

Overexpression of cysE has been suggested in WO 2007/077041, which is incorporated by reference into this application.

Production of methionine may be further increased by using an altered metB allele that uses preferentially or exclusively $H_2S$ and thus produces homocysteine from 0-succinyl-homoserine as has been described in the patent application WO 2004/076659 that is incorporated herein by reference.

A further increase in the production of L-methionine in E. coli, its precursors or compounds derived thereof, is achieved by attenuating or deleting the gene for the repressor protein MetJ (GenBank 1790373), responsible for the down-regulation of the methionine regulon as was suggested in patent application JP 2000/157267. In Corynebacterium the master sulphur regulator McbR (AAP45010) should be deleted as indicated in WO2007/012078.

In another specific embodiment of the invention, the production of the byproduct isoleucine is reduced. Isoleucine is an amino acid that can be separated from methionine only with great difficulty increasing drastically the cost for the production of pure methionine. In addition, the production of isoleucine consumes carbon that could be used for the production of methionine. Therefore it is desirable that the production of isoleucine is kept as low as possible.

Isoleucine is produced either via the threonine biosynthesis pathway or via a reaction of γ-elimination of O-succinylhomoserine, in the absence of cysteine.

Means to reduce γ-elimination activity have been described in the patent applications WO 2006/082254 and WO 2007/077041 that are incorporated by references into this application.

Isoleucine production is below the detection level (HPLC) in a non-modified microorganism such as E. coli. In the modified microorganism, the produced amount can reach 2% g isoleucine/g glucose. The quantity of isoleucine recovered in the medium may be greater than 40 mM.

The inventors have shown that the overexpression of at least one of the following genes involved in serine biosynthesis also reduces the production of isoleucine.

| gene | E. coli | C. glutamicum | function |
|---|---|---|---|
| serA | 1789279 | YP_22557 | phosphoglycerate dehydrogenase, |
| serB | 1790849 | YP_226764 | phosphoserine phosphatase |
| serC | 1787136 | YP_225120 | phosphoserine aminotransferase |

In a more specific embodiment of the invention the inventors have demonstrated that enhanced expression of serA, serB and/or serC reduces the production of the byproduct isoleucine.

In another specific embodiment of the invention, the production of the byproduct homolanthionine is reduced. Homolanthionine is an amino acid that is produced form activated homoserine and homocysteine (Kromer et al (2006) J Bacteriol 188, 609-18; and patent application WO 2007/051725 by BASF). Homolanthionine is an amino acid that can be separated from methionine only with great difficulty increasing drastically the cost for the production of pure methionine. In addition, homolanthionine comprises two aspartate derived homoserine molecules and a reduced sulfur molecule, all of which could increase methionine/ carbon source yield, if transformed into methionine. Therefore it is desirable that the production of homolanthionine is kept as low as possible and the used precursors are transformed into methionine. The PCT application WO 2007/051725 proposes some means to reduce the production of homolanthionine. The inventors have found other means to reduce the production of homolanthionine that at the same time permit the transformation of the substrate homocysteine to methionine. Means that favor the transformation of homocysteine to methionine specifically are the attenuation of the formyl-THF deformylase activity encoded by the purU gene, the overexpression of methylene-THF reductase activity encoded by the metF gene, the attenuation of the expression of the pykA and/or pykF gene, the overexpression of serA, serB or serC or the overexpression of the lpd gene.

The sulfur source used for the fermentative production of L-methionine, its precursors or compounds derived thereof, may be any of the following: sulfate, thiosulfate, hydrogen sulfide, dithionate, dithionite, sulfite or a combination thereof.

In a preferred embodiment of the invention, the sulfur source is sulfate and/or thiosulfate.

As the preferred carbon source, the inventors recommend glucose or sucrose.

The invention also concerns the process for the production of L-methionine, its precursors or compounds derived thereof, comprising the fermentation of the methionine producing microorganism described above, the concentration of methionine, its precursors or derivatives and the isolation of the desired product(s) of the fermentation broth.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum* and about 37° C. for *E. coli*.

The fermentation is generally conducted in fermenters with an inorganic culture medium of known defined composition adapted to the bacteria used, containing at least one simple carbon source, and if necessary a co-substrate necessary for the production of the metabolite.

In particular, the inorganic culture medium for *E. coli* can be of identical or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

Analogously, the inorganic culture medium for *C. glutamicum* can be of identical or similar composition to BMCG medium (Liebl et al., 1989, *Appl. Microbiol. Biotechnol.* 32: 205-210) or to a medium such as described by Riedel et al. (2001, *J. Mol. Microbiol. Biotechnol.* 3: 573-583). The media can be supplemented to compensate for auxotrophies introduced by mutations.

After fermentation L-methionine, its precursors or compounds derived thereof, is/are recovered and purified if necessary. The methods for the recovery and purification of the produced compound such as methionine and N-acetyl-methionine in the culture media are well known to those skilled in the art.

Optionally, from 0 to 100%, preferentially at least 90%, more preferentially 95%, even more preferentially at least 99% of the biomass may be retained during the purification of the fermentation product.

Optionally, the methionine derivative N-acetyl-methionine is transformed into methionine by deacylation, before methionine is recovered.

The invention also relates to a microorganism that is optimized for the fermentative production of methionine, i.e. having an improved methionine/carbon source yield compared to a non-modified microorganism, and that comprises the genetic modifications described above.

DRAWINGS

FIG. 1

Methionine biosynthesis in *E. coli*. Abbreviation: P phosphate, GA3P glyceraldehyde-3-phosphate, PGA phosphoglycerate, PEP phosphoenolpyruvate, Pyr pyruvate, Asp aspartate, Asp-P aspartylphosphate, Asp-SA aspartatesemialdehyde, homoser homoserine, OSH O-succinylhomoserine, γ-cys γ-cystathionine, homocys homocysteine, homolan homolanthionine, THF tetrahydrofolate, Ser serine, Cyst Cysteine, Gly glycine, PPP pentose phosphate shunt.

FIG. 2:

Evolution of $OD_{600\ nm}$ and $Y_{met+NAM}$ for the strain1 PtrcF-cysPUWAM PtrcF-cysJIH ΔpykF ΔpykA Ptrc09-gcvTHP grown under three different culture conditions: growth with phosphate excess (solid symbols), growth with phosphate starvation at 100 $UOD_{600\ nm}$ (blank symbols) and growth with phosphate limitation (grey symbols).

DETAILED DESCRIPTION OF THE INVENTION

An *E. coli* strain in which the methionine repressor encoded by the metJ gene has been replaced by a chloramphenicol cassette (ΔmetJ::Cm) and that harbors a metA allele with reduced feed-back sensitivity to methionine and SAM (metA*11) has been described in PCT WO2005108561 filed on May 12, 2004. Overexpression of the genes metF and metH from artificial promoters integrated upstream of the structural genes into the chromosome (Ptrc-metF, Ptrc-metH) has been described in patent application WO 2007/077041. This document also describes the overexpression of an aspartokinase/homoserine dehydrogenase with reduced feed-back inhibition to threonine (thrA*) and the overexpression of serine acetyl-transferase (cysE) and the metA*11 from the plasmid pME101. A strain with all modifications described in the above patent applications, called strain1 in this application, has the genotype ΔmetJ metA*11 Ptrc-metH Ptrc-metF (pME101-thrA*1-cysE-PgapA-metA*11). All subsequent constructions described below are based on these constructs.

Construction of Strains Overexpressing the Operons cysPUWAM, cysJIH, gcvTHP and the Genes metF, serA, serC, serB, glyA and lpd, and Strains with Deletions of the Genes pykA, pykF and purU All constructs with the exception of metF were initially prepared in the *E. coli* strain MG1655 and subsequently transferred into the final strain by transduction.

Construction of MG1655 Ptrc-cysPUWAM

To put the operon cysPUWAM under the control of the heterologous Ptrc promoter, the homologous recombination strategy described by Datsenko & Wanner (2000) was used. This strategy allows the insertion of a chloramphenicol or a kanamycin resistance cassette together with the heterologous promoter upstream of the genes concerned. For this purpose the following oligonucleotides were used:

```
Ptrc-cysPUWAM F
                                                  (SEQ ID NO 1)
GCGCGAGTGAGTTCTTTTTCAGTAAGTTAACGGCCATTGCGCACCC

TTATAAATTTAATGACTTTCTTCCACACATTATACGAGCCGGATGA

TTAATTGTCAACAGCTTGTAGGCTGGAGCTGCTTCG
``` with
a region (upper case) homologous to the sequence (2541512-2541578) of the gene cysP (reference sequence on the EcoGene website),
a region (upper bold case) for the amplification of the chloramphenicol resistance cassette (reference sequence in Datsenko, K. A. & Wanner, B. L., 2000, PNAS, 97: 6640-6645),
a region (upper italic case) for the trc promoter sequence with the −35 and −10 box underlined

```
Ptrc-cysPUWAM R
                                                  (SEQ ID NO 2)
CCAAATCACCAAACGGTATATAAAACCGTTACTCCTTTCACGTCCGTTAT

AAATATGATGGCTATTATCACACTGGCTCACCTTCGGGTGGGCCTTTCTG

CCATATGAATATCCTCCTTAG
``` with
a region (upper case) homologous to the sequence (2541644-2541578) of the region upstream of the gene cysP (reference sequence on the EcoGene website),
a region (upper bold case) for the amplification of the chloramphenicol resistance cassette (reference sequence in Datsenko, K. A. & Wanner, B. L., 2000, PNAS, 97: 6640-6645),
a region (upper italic underlined case) for the bacteriophage T7 terminator sequence (Genbank V01146)
The oligonucleotides Ptrc-cysPUWAM F and Ptrc-cysPUWAM R were used to amplify the chloramphenicol resistance cassette from the plasmid pKD3. The obtained PCR product was then introduced into the strain MG1655 (pKD46) by electroporation. In this strain the Red recombinase enzyme was expressed and permitted homologous recombination. Chloramphenicol resistant transformants were then selected and the insertion of the resistance cassette was verified by PCR analysis with the oligonucleotides Ptrc-cysPUWAMRv and Ptrc-cysPUWAMFv shown below. The strain retained was designated MG1655 Ptrc-cysPUWAM:Cm.

```
Ptrc-cysPUWAMRv (SEQ ID NO 3):
GCAGGATTTGTACGTCGGTCACC (homologous to the sequence from 2541260 to 2541282).

Ptrc-cysPUWAMFv (SEQ ID NO 4):
cgtcttgaactaagttcaccaggc (homologous to the sequence from 2541812 to 2541789).
```

Construction of MG1655 Ptrc-cysJIH

To put the operon cysJIH under the control of the heterologous Ptrc promoter, the homologous recombination strategy described by Datsenko & Wanner (2000) was used. This strategy allows the insertion of a chloramphenicol or a kanamycin resistance cassette together with the heterologous promoter upstream of the genes concerned. For this purpose the following oligonucleotides were used:

```
PtrcF-cysJIH R
                                                  (SEQ ID NO 5)
CCAGTAAGCAAAGCTGTTTCTGCGCCCTGTCAGCGCCCATAAAACAGAAG

AGATTCCACACATTATACGAGCCGGATGATTAATTGTCAACAGCTTGTAG

GCTGGAGCTGCTTCG
``` with
a region (upper case) homologous to the sequence (2889935-2889987) of the gene cysJ (reference sequence on the EcoGene website),
a region (upper bold case) for the amplification of the kanamycin resistance cassette (reference sequence in Datsenko, K. A. & Wanner, B. L., 2000, PNAS, 97: 6640-6645),
a region (upper italic case) for the trc promoter sequence with the −35 and −10 box underlined

```
PtrcF-cysJIH F
                                                  (SEQ ID NO 6)
GGTTATTAGTTATCGCTATCCCGTCTTTAATCCACACCGTTTGCCCCGTT

AACCTTACCTTCACACTGGCTCACCTTCGGGTGGGCCTTTCTGCCATATG

AATATCCTCCTTAG
``` with
a region (upper case) homologous to the sequence (2890047-2889988) of the region upstream of the gene cysJ (reference sequence on the EcoGene website),
a region (upper bold case) for the amplification of the kanamycin resistance cassette (reference sequence in Datsenko, K. A. & Wanner, B. L., 2000, PNAS, 97: 6640-6645),
a region (upper italic underlined case) for the bacteriophage T7 terminator sequence (Genbank V01146)
The oligonucleotides PtrcF-cysJIH F and PtrcF-cysJIH R were used to amplify the kanamycin resistance cassette from the plasmid pKD4. The obtained PCR product was then introduced into the strain MG1655 (pKD46) by electroporation. In this strain the Red recombinase enzyme was expressed and permitted the homologous recombination. Kanamycin resistant transformants were then selected and the insertion of the resistance cassette was verified by a PCR analysis with the oligonucleotides Ptrc-cysJIHFv and Ptrc-cysJIHRv shown below. The strain retained was designated MG1655 Ptrc-cysJIH:Km.

```
Ptrc-cysJIHFv (SEQ ID NO 7):
GCAGTTCGACAAGTTCTTTCACC (homologous to the sequence from 2889042 to 2889064).

Ptrc-cysJIHRv (SEQ ID NO 8):
CCAGAACACAACACCCTAACATAGCG (homologous to the sequence from 2890663 to 2890638).
```

Construction of MG1655 Ptrc09-gcvTHP

To put the operon gcvTHP under the control of the heterologous Ptrc promoter, the homologous recombination strategy described by Datsenko & Wanner (2000) was used. This strategy allows the insertion of a chloramphenicol or a kanamycin resistance cassette together with the heterologous promoter upstream of the genes concerned. For this purpose the following oligonucleotides were used:

Ptrc-gcvTHP F
(SEQ ID NO 9)
CCACCATGCGAGCGCCGCAAAGCGTGTGTTGTTCGTACAAAGGAGTCTGT

TGTGCCATAATATA*CCTCCT*TATTCCACAC*ATTATA*CGAGCCGGATGATT

AA*TTGTCAA*CAGCTCTGTAGGCTGGAGCTGCTTCG with a region (upper case) homologous to the sequence (3048630-3048687) of the gene gcvT (reference sequence on the EcoGene website), a region (upper bold case) for the amplification of the kanamycin resistance cassette (reference sequence in Datsenko, K. A. & Wanner, B. L., 2000, PNAS, 97: 6640-6645), a region (upper italic case) for the trc promoter sequence with the −35 and −10 box underlined Ptrc-gcvTHP R
(SEQ ID NO 10)
CTGTCGCGATTTTTGCATTTTTTAACCATAAGCTAATGTGATGATCAATT

TTACCTTACATATGAATATCCTCCTTAG with a region (upper case) homologous to the sequence (3048887-3048830) of the region upstream of the gene gcvT (reference sequence on the EcoGene website), a region (upper bold case) for the amplification of the kanamycin resistance cassette (reference sequence in Datsenko, K. A. & Wanner, B. L., 2000, PNAS, 97: 6640-6645), The oligonucleotides Ptrc-gcvTHP F and Ptrc-gcvTHP R were used to amplify the kanamycin resistance cassette from the plasmid pKD4. The obtained PCR product was then introduced by electroporation into the strain MG1655 (pKD46). In this strain the Red recombinase enzyme was expressed and permitted the homologous recombination. Kanamycin resistant transformants were then selected and the insertion of the resistance cassette was verified by a PCR analysis with the oligonucleotides Ptrc-gcvTHP F2 and Ptrc-gcvTHP R2 shown below. The strain retained was designated MG1655 PtrcgcvTHP:Km.
Ptrc-gcvTHP F2 (SEQ ID NO 11):
CTATCACACCGCCAGAGGCATTC (homologous to the sequence from 3048399 to 3048421).

Ptrc-gcvTHP R2 (SEQ ID NO 12):
CCCATCACACTTTCATCTCCCG (homologous to the sequence from 3049106 to 3049085).

Construction of MG1655 ΔpykA

To delete the pykA gene, the homologous recombination strategy described by Datsenko & Wanner (2000) was used. This strategy allows the insertion of a chloramphenicol or a kanamycin resistance cassette into the genes concerned. For this purpose the following oligonucleotides were used:

DpykA F
(SEQ ID NO 13)
cgcggcgggtgccaacgttgtacgtatgaactttctcacggctcgcctg aagatcacaaaatgcgcgcggataaagttcgTGTAGGCTGGAGCTGCTTC

G with a region (lower case) homologous to the sequence (1935756-1935838) of the pykA region (reference sequence on the EcoGene website), a region (upper bold case) for the amplification of the chloramphenicol resistance cassette (reference sequence in Datsenko, K. A. & Wanner, B. L., 2000, PNAS, 97: 6640-6645), DpykA R
(SEQ ID NO 14)
CGCCGCATCCGGCAACGTACTTACTCTACCGTTAAAATACGCGTGGTATT

AGTAGAACCCACGGTACTCATCACGTCGCCCCATATGAATATCCTCCTTA

G with a region (upper case) homologous to the sequence (1937135-1937055) of the pykA region (reference sequence on the EcoGene website), a region (upper bold case) for the amplification of the chloramphenicol resistance cassette (reference sequence in Datsenko, K. A. & Wanner, B. L., 2000, PNAS, 97: 6640-6645), The oligonucleotides DpykA F and DpykA R were used to amplify the chloramphenicol resistance cassette from the plasmid pKD3. The obtained PCR product was then introduced by electroporation into the strain MG1655 (pKD46). In this strain the Red recombinase enzyme was expressed and permitted the homologous recombination. Chloramphenicol resistant transformants were then selected and the insertion of the resistance cassette was verified by a PCR analysis with the oligonucleotides pykA F and pykA R shown below. The strain retained was designated MG1655 ΔpykA::Cm.

PykA F (SEQ ID NO 15):
ggcaattaccctcgacgtaccgg (homologous to the sequence from 1935338 to 1935360).

PykA R (SEQ ID NO 16):
ccgcctctaacagatcatccatcgg (homologous to the sequence from 1935401 to 1937425).

Construction of MG1655 ΔpykF

To delete the pykF gene, the homologous recombination strategy described by Datsenko & Wanner (2000) was used. This strategy allows the insertion of a chloramphenicol or a kanamycin resistance cassette into the genes concerned. For this purpose the following oligonucleotides were used:

DpykF F
(SEQ ID NO 17)
cccatccttctcaacttaaagactaagactgtcatgaaaaagaccaaaat tgtttgcaccatcggaccgaaaaccgaaTGTAGGCTGGAGCTGCTTCG with a region (lower case) homologous to the sequence (1753689-1753767) of the pykF region (reference sequence on the EcoGene website), a region (upper bold case) for the amplification of the kanamycin resistance cassette (reference sequence in Datsenko, K. A. & Wanner, B. L., 2000, PNAS, 97: 6640-6645), DpykF R
(SEQ ID NO 18)
ggacgtgaacagatgcggtgttagtagtgccgctcggtaccagtgcacca gaaaccataactacaacgtcacctttgtgCATATGAATATCCTCCTTAG with a region (upper case) homologous to the sequence (1755129-1755051) of the pykF region (reference sequence on the EcoGene website), a region (upper bold case) for the amplification of the kanamycin resistance cassette (reference sequence in Datsenko, K. A. & Wanner, B. L., 2000, PNAS, 97: 6640-6645), The oligonucleotides DpykF F and DpykF R were used to amplify the kanamycin resistance cassette from the plasmid pKD4. The obtained PCR product was then introduced by electroporation into the strain MG1655 (pKD46). In this strain the Red recombinase enzyme was expressed and permitted the homologous recombination. Kanamycin resistant transformants were then selected and the insertion of the resistance cassette was verified by a PCR analysis with the oligonucleotides pykF F and pykF R shown below. The strain retained was designated MG1655 DpykF::Km.

```
PykF F (SEQ ID NO 19):
gcgtaaccttttccctggaacg (homologous to the sequence from 1753371 to 1753392).

PykF R (SEQ ID NO 20):
gcgttgctggagcaacctgccagc (homologous to the sequence from 1755518 to 1755495).
```

Construction of MG1655 ΔpurU

To delete the purU gene, the homologous recombination strategy described by Datsenko & Wanner (2000) was used. This strategy allows the insertion of a chloramphenicol or a kanamycin resistance cassette into the genes concerned. For this purpose the following oligonucleotides were used:

DpurU F
(SEQ ID NO 21)
ggtaaaaaatttaaaaagtgctgcggccaataatggttgacggtacggtt tagcaaacactctcaacaaggttatccagcTGTAGGCTGGAGCTGCTTCG with a region (lower case) homologous to the sequence (1287929-1287849) of the purU region (reference sequence on the EcoGene website), a region (upper bold case) for the amplification of the kanamycin resistance cassette (reference sequence in Datsenko, K. A. & Wanner, B. L., 2000, PNAS, 97: 6640-6645), DpurU R
(SEQ ID NO 22)
ggttgcgtaattttcatccgtaacggattaaaggtaaccagttaUtttgc
tggcgattaaagaataatcgttcgattaccCATATGAATATCCTCCTTAG with a region (upper case) homologous to the sequence (1286948-1287028) of the purU region (reference sequence on the EcoGene website), a region (upper bold case) for the amplification of the kanamycin resistance cassette (reference sequence in Datsenko, K. A. & Wanner, B. L., 2000, PNAS, 97: 6640-6645), The oligonucleotides DpurU F and DpurU R were used to amplify the kanamycin resistance cassette from the plasmid pKD4. The obtained PCR product was then introduced by electroporation into the strain MG1655 (pKD46). In this strain the Red recombinase enzyme was expressed and permitted the homologous recombination. Kanamycin resistant transformants were then selected and the insertion of the resistance cassette was verified by a PCR analysis with the oligonucleotides purU F and purU R shown below. The strain retained was designated MG1655 DpurU::Km.

```
PurU F (SEQ ID NO 23):
ggaatgcaatcgtagccacatcgc (homologous to the
sequence from 1288447 to 1288424).

PurU R (SEQ ID NO 24):
gcggattcgttgggaagttcaggg (homologous to the
sequence from 1286129 to 1286452).
```

Construction pCC1BAC-serA-serC

To increase the expression of the serA and serC genes, the gene dosage of the two genes was increased in the methionine producing cell by expressing the enzymes from the copy control vector pCC1BAC (Epicentre) using their proper promoters.

For this purpose, first the serC gene was amplified from the E. coli genome using the oligonucleotides -serC F (XbaI) and serC R (HindIII). The PCR product was restricted using enzymes XbaI and HindIII and cloned into the vector pUC18 (Stratagene) restricted by the same restriction enzymes. The resulting vector was named pUC18-serC.

```
serC F(XbaI) (SEQ ID NO 25):
tgcTCTAGAgtccgcgctgtgcaaatccagaatgg
``` with a region (lower case) homologous to the sequence (956619-956644) of the gene serC (reference sequence on the EcoGene website), a region (upper bold case) harbouring the XbaI site

```
serC R (HindIII) (SEQ ID NO 26):
cccAAGCTTAACTCTCTACAACAGAAATAAAAAC
``` with a region (upper case) homologous to the sequence (958028-958004) of the gene serC (reference sequence on the EcoGene website), a region (upper bold case) harbouring the HindIII site Subsequently the serA gene was amplified from the E. coli genome using the oligonucleotides serA F (XbaI) and serA R (SmaI-HindIII). The PCR product was restricted using enzymes XbaI and SmaI and cloned into the vector pUC18-serC restricted by the same restriction enzymes. The resulting vector was verified by sequencing and called pUC18-serA-serC.

```
serA F (XbaI) (SEQ ID NO 27):
ctagTCTAGAttagtacagcagacgggcgcg
``` with a region (lower case) homologous to the sequence (3055198-3055218) of the gene serA (reference sequence on the EcoGene website), a region (upper case) harbouring the XbaI site

```
serA R (SmaI-HindIII) (SEQ ID NO 28):
    tccCCCGGGaagcttCCGTCAGGGCGTGGTGACCG
``` with
- a region (upper case) homologous to the sequence (3056878-3056859) of the gene serA (reference sequence on the EcoGene website),
- a region (bold case) harbouring the SmaI and HindIII sites To transfer the genes serA and serC into the copy control vector pCC1BAC, the vector pUC18-serA-serC was restricted with the enzyme HindIII and cloned into HindIII cloning ready pCC1BAC (Epicentre).
The resulting construct was verified and called pCC1BAC-serA-serC.

Construction of the Vector pCC1BAC-serB-serA-serC
To increase the expression of the serA, serB and serC genes, the gene dosage of the three genes was increased in the methionine producing cell by expressing the enzymes from the copy control vector pCC1BAC (Epicentre) using their proper promoters.
For this purpose, the serB gene was amplified from the *E. coli* genome using the oligonucleotides serB (SphI) and serB (SmaI). The PCR product was restricted using enzymes SphI and SmaI and cloned into the vector pUC18-serA-serC restricted by the same restriction enzymes. The resulting vector was named pUC18-serB-serA-serC.

```
serB (SphI) (SEQ ID NO 29):
    atgcGCATGCCCACCCTTTGAAAATTTGAGAC
``` with
- a region (upper case) homologous to the sequence (4622362-4622383) of the gene serB (reference sequence on the EcoGene website),
- a region (upper underlined case) harbouring the SphI site

```
serB (SmaI) (SEQ ID NO 30):
gcatgtcgacatCCCGGGGCAGAAAGGCCCACCCGAAGGTGAGCCAGT
GTGATTACTTCTGATTCAGGCTGCC
``` with
- a region (upper case) homologous to the sequence (4623433-4623412) of the gene serB (reference sequence on the EcoGene website),
- a region (upper underlined case) harbouring the SmaI site
- a region (upper italic case) for the bacteriophage T7 terminator sequence (Genbank V01146)

To transfer the genes serA, serB and serC into the copy control vector pCC1BAC, the vector pUC18-serB-serA-serC was restricted with the enzyme HindIII and cloned into HindIII cloning ready pCC1BAC (Epicentre).
The resulting construct was verified and called pCC1BAC-serB-serA-serC.

Construction of the vector pCC1BAC-serB-glyA-serA-serC
To increase the expression of the serA, serB, serC and glyA genes, the gene dosage of the three genes was increased in the methionine producing cell by expressing the enzymes from the copy control vector pCC1BAC (Epicentre) using their proper promoters.
For this purpose, the glyA gene was amplified from the *E. coli* genome using the oligonucleotides PglyA F (HindIII) and glyA R (EcoRI-HindIII). The PCR product was restricted using enzyme HindIII, blunted with the Klenow fragment and cloned into the vector pUC18-serB-serA-serC restricted by the restriction enzyme SmaI. The resulting vector was named pUC18-serB-glyA-serA-serC.

```
PglyA F (HindIII) (SEQ ID NO 31):
    TCATCGGATCCATCAAGCTTGAAAGAATGTGATGAAGTG
``` with
- a region (upper bold case) homologous to the sequence (2683760-2683742) of the glyA region (reference sequence on the EcoGene website),
- a region (upper underlined case) harbouring the HindIII site

```
glyA R (EcoRI-HindIII) (SEQ ID NO 32):
ATCTAGTAAGCTTAGTGAATTCGTTACGACAGATTTGATGGCGCG
``` with
- a region (upper italic case) homologous to the sequence (2682084-2682061) of the glyA region (reference sequence on the EcoGene website),
- a region (upper underlined case) harbouring the HindIII and EcoRI sites To transfer the genes serA, serB, serC and glyA into the copy control vector pCC1BAC, the vector pUC18-serB-glyA-serA-serC was restricted with the enzyme HindIII and cloned into HindIII cloning ready pCC1BAC (Epicentre).
The resulting construct was verified and called pCC1BAC-serB-glyA-serA-serC.

Construction of the vector pJB137-lpd
The lpd gene was amplified from the *E. coli* genome using the oligonucleotides lpd F (HindIII) and lpd R (EcoRI). The PCR product was restricted using enzymes EcoRI and HindIII and cloned into the vector pJB137 restricted by the same restriction enzymes. The resulting vector was named pJB137-lpd.

```
lpd F (HindIII) (SEQ ID NO 33):
    atgcgctaAAGCTTGGTTATTAGCGAATAGACAAATCGG
``` with
- a region (upper case) homologous to the sequence (127644-127668) of the gene lpd (reference sequence on the EcoGene website),
- a region (upper bold case) harbouring the HindIII site

```
lpd R (EcoRI) (SEQ ID NO 34):
    gcatgatcGAATTCTGCAGACGTAAAAAAAGCGGCGTGG
``` with
- a region (upper case) homologous to the sequence (129404-129380) of the gene lpd (reference sequence on the EcoGene website),
- a region (upper bold case) harbouring the EcoRI site The resulting construct was verified and called pJB137-lpd.

Integration of Individual Mutations into Strain1
Subsequently the following strains were derived from strain ΔmetJ metA*11 Ptrc-metH Ptrc-metF by P1 phage transduction and removal of resistance cassettes when required.

Strains Constructed
ΔmetJ metA*11 Ptrc-metH Ptrc-metF PtrcF-cysPUWAM PtrcF-cysJIH
ΔmetJ metA*11 Ptrc-metH Ptrc-metF PtrcF-cysPUWAM PtrcF-cysJIH
ΔmetJ metA*11 Ptrc-metH Ptrc-metF PtrcF-cysPUWAM PtrcF-cysJIH ΔpykF ΔpykA ΔmetJ metA*11 Ptrc-metH Ptrc-metF PtrcF-cysPUWAM PtrcF-cysJIH ΔpykF ΔpykA Ptrc09-gcvTHP ΔmetJ metA*11 Ptrc-metH Ptrc-metF PtrcF-cysPUWAM PtrcF-cysJIH ΔpykF ΔpykA Ptrc09-gcvTHP ΔpurU ΔmetJ metA*11 Ptrc-metH Ptrc-metF PtrcF-cysPUWAM PtrcF-cysJIH ΔpykF ΔpykA Ptrc09-gcvTHP Ptrc36-ARNmst17-metF ΔmetJ metA*11 Ptrc-metH Ptrc-metF PtrcF-cysPUWAM PtrcF-cysJIH ΔpykF ΔpykA Ptrc09-gcvTHP ΔpurUPtrc36-ARNmst17-metF Transfer via P1 transduction and removal of antibiotic resistance cassettes will be exemplified by the strain ΔmetJ metA*11 Ptrc-metH Ptrc-metF PtrcF-cysPUWAM::Cm PtrcF-cysJIH::Km. All other constructs except for strains containing Ptrc36-ARNmst17-metF (see below) were constructed in a similar manner.

To transfer the promoter construct PtrcF-cysPUWAM::Cm into the strain MG1655 ΔmetJ metA*11 Ptrc-metH Ptrc-metF, the method of phage P1 transduction was used. The protocol followed was implemented in 2 steps with the preparation of the phage lysate of the strain MG1655 PtrcF-cysPUWAM::Cm and the subsequent transduction into strain MG1655 ΔmetJ metA*11 Ptrc-metHPtrc-metF Preparation of Phage Lysate P1:
Inoculation with 100 µl of an overnight culture of the strain MG1655 PtrcF-cysPUWAM::Cm of 10 ml of LB+Km 50 µg/ml+glucose 0.2%+CaCl$_2$ 5 mM.
Incubation for 30 min at 37° C. with shaking.
Addition of 100 µl of phage lysate P1 prepared on the strain MG1655 (about $1.10^9$ phage/ml)
Shaking at 37° C. for 3 hours until all cells were lysed.
Addition of 200 µl chloroform and vortexing.
Centrifugation for 10 min at 4500 g to eliminate cell debris.
Transfer of the supernatant to a sterile tube and addition of 200 µl chloroform.
Storage of lysate at 4° C.
Transduction
Centrifugation for 10 min at 1500 g of 5 ml of an overnight culture of the strain MG1655 ΔmetJ metA*11 Ptrc-metH Ptrc-metF in LB medium.
Suspension of the cell pellet in 2.5 ml of 10 mM MgSO$_4$, 5 mM CaCl$_2$
Control tubes: 100 µl cells
  100 µl phages P1 of strain MG1655 PtrcF-cysPUWAM::Cm
Test tube: 100 µl of cells+100 µl of phages P1 of the strain MG1655
PtrcF-cysPUWAM::Cm
Incubation for 30 min at 30° C. without shaking.
Addition of 100 µl of 1 M sodium citrate in each tube and vortexing.
Addition of 1 ml of LB
Incubation for 1 hour at 37° C. with shaking
Spreading on dishes LB+Cm 50 µg/ml after centrifuging of tubes for 3 min at 7000 rpm.
Incubation at 37° C. overnight.
Verification of the Strain Chloramphenicol resistant transformants were selected and the presence of the promoter construct MG1655 PtrcF-cysPUWAM::Cm was verified by PCR analysis with the oligonucleotides described above for the verification of the strain MG1655 PtrcF-cysPUWAM::Cm. The strain retained was designated ΔmetJ metA*11 Ptrc-metH Ptrc-metF PtrcF-cysPUWAM::Cm. Subsequently the PtrcF-cysJIH allele was introduced using the P1 transduction procedure as described above. The resulting strain was named ΔmetJ metA*11 Ptrc-metH Ptrc-metF PtrcF-cysPUWAM::Cm PtrcF-cysJIH::Km.

For the introduction of the pykA and pykF deletions the resistance cassettes were eliminated from the strain DmetJ metA*11 Ptrc-metH Ptrc-metF PtrcF-cysPUWAM::Cm PtrcF-cysJIH::Km.

For this purpose the plasmid pCP20 carrying FLP recombinase acting at the FRT sites of the resistance cassettes was introduced into the recombinant strain by electroporation. After a series of cultures at 42° C., the loss of the two cassettes was verified by PCR analysis. The strain retained was designated ΔmetJ metA*11 Ptrc-metH Ptrc-metF PtrcF-cysPUWAM PtrcF-cysJIH. Then the deletions of the pykA and pykF alleles could be introduced via P1 transduction. Similarly the deletion of the purU gene and the glycine cleavage complex overexpression construct Ptrc09-gcvTHP were introduced after the elimination of the corresponding cassettes.

For reasons of proximity the construct Ptrc36-ARNmst17-metF could not be introduced by P1 transduction and was constructed by introduction via PCR.

For this purpose the homologous recombination strategy described by Datsenko & Wanner (2000) was used. This strategy allows the insertion of a chloramphenicol or a kanamycin resistance cassette near the genes concerned. For this purpose the following oligonucleotides were used:

Ptrc36-ARNmst-metF
(SEQ ID NO 35)
(GGCTCTGATTCAGGGCATCCCGCTGGCTGGCGTGAAAAAAGCTCAT
AATATACCTCCTcgtcaacaatatctcactcgagataactccaccTA
TTCCACACATTATACGAGCCGG Capital letter bold: Ribosome binding site and -10 region
Small letter: RNA stabilizing sequence
Capital italics: part of the Ptrc promoter Ptrc-metF F
(SEQ ID NO 36)
ccttcatctttacatctggacgtctaaacggatagatgtgcacaacac
aacatataactacaagcgattgatgaggtaaggttcacactggctcac
cttcgggtgggcctttctgcCATATGAATATCCTCCTTAG with:
a region (lower case) homologous to the sequence (4130114-4130195) of the region of gene metF (reference sequence on the GenoList website),
a region (italics, lower case) homologous to the sequence of the bacteriophage T7 terminus (Genbank V01146)
a region (upper case) for the amplification of the kanamycin resistance cassette (reference sequence in Datsenko, K. A. & Wanner, B. L., 2000, PNAS, 97: 6640-6645), For the PCR DNA isolated from MG1655 metA*11 DmetJ::Cm Ptrc-metF::Km described in patent application WO 2007077041 was used as matrix.

The oligonucleotides Ptrc-metF F and Ptrc36-ARNmst-metF were used to amplify the kanamycin resistance cassette from the plasmid pKD4. The PCR product obtained was then introduced by electroporation into the strain ΔmetJ metA*11 Ptrc-metH Ptrc-metF PtrcF-cysPUWAM PtrcF-cysJIH ΔpykF ΔpykA Ptrc09-gcvTHP ΔpurU (pKD46), in which the Red recombinase enzyme expressed permits the homologous recombination. The kanamycin resistant transformants were selected and the insertion of the resistance cassette was verified by a PCR analysis with the oligonucleotides Ptrc-metFv F and Ptrc-metFv R defined below.

Ptrc-metFv F (SEQ ID NO 37):
GCCCGGTACTCATGTTTTCGGGTTTATGG
(homologous to the sequence from 4129866 to 4129894).

Ptrc-metFv R (SEQ ID NO 38):
CCGTTATTCCAGTAGTCGCGTGCAATGG
(homologous to the sequence from 4130524 to 4130497).

The resulting strain was called ΔmetJ metA*11 Ptrc-metH Ptrc-metF PtrcF-cysPUWAM PtrcF-cysJIH ΔpykF ΔpykA Ptrc09-gcvTHP ΔpurU Ptrc36-ARNmst17-metF:Km.

Subsequently the plasmid (pME101-thrA*1-cysE-PgapA-metA*11) was introduced into the above described strains yielding strains:
strain1 PtrcF-cysPUWAM PtrcF-cysJIH
strain1 PtrcF-cysPUWAM PtrcF-cysJIH ΔpykF ΔpykA
strain1 PtrcF-cysPUWAM PtrcF-cysJIH ΔpykF ΔpykA Ptrc09-gcvTHP
strain1 PtrcF-cysPUWAM PtrcF-cysJIH ΔpykF ΔpykAPtrc09-gcvTHP ΔpurU
strain1 PtrcF-cysPUWAM PtrcF-cysJIH ΔpykF ΔpykA Ptrc09-gcvTHP Ptrc36-ARNmst17-metF
strain1 PtrcF-cysPUWAM PtrcF-cysJIH ΔpykF ΔpykA Ptrc09-gcvTHP ΔpurU Ptrc36-ARNmst17-metF
Into certain strains the plasmids pJB137-lpd, pCC1BAC-serA-serC, pCC1BAC-serB-serA-serC or pCC1BAC-serB-glyA-serA-serC were introduced yielding:
strain1 PtrcF-cysPUWAM PtrcF-cysJIH ΔpykF ΔpykA Ptrc09-gcvTHP (pJB137-lpd)
strain1 PtrcF-cysPUWAM PtrcF-cysJIH ΔpykF ΔpykA Ptrc09-gcvTHP ΔpurU (pCC1 BAC-serA-serC)
strain1 PtrcF-cysPUWAM PtrcF-cysJIH ΔpykF ΔpykA Ptrc09-gcvTHP ΔpurU Ptrc36-ARNmst17-metF (pCC1BAC-serA-serC)
strain1 PtrcF-cysPUWAM PtrcF-cysJIH ΔpykF ΔpykA Ptrc09-gcvTHP ΔpurU Ptrc36-ARNmst17-metF (pCC1BAC-serB-serA-serC)
strain1 PtrcF-cysPUWAM PtrcF-cysJIH ΔpykF ΔpykA Ptrc09-gcvTHP ΔpurU Ptrc36-ARNmst17-metF (pCC1BAC-serB-glyA-serA-serC)

Evaluation of Methionine Producing Strains

Production strains were initially evaluated in small Erlenmeyer flasks. A 5.5 mL preculture was grown in a mixed medium (10% LB medium (Sigma 25%) with 2.5 g·L$^{-1}$ glucose and 90% minimal medium PC1) and was used to inoculate a 50 mL culture to an OD$_{600}$ of 0.2 in medium PC1. Kanamycin and spectinomycin were added if necessary at a concentration of 50 mg·L$^{-1}$, chloramphenicol at 30 mg·L$^{-1}$. When the culture had reached an OD$_{600}$ of 6 to 7, extracellular amino acids were quantified by HPLC after OPA/Fmoc derivatization and other relevant metabolites were analyzed using HPLC with refractometric detection (organic acids and glucose) and GC-MS after silylation.

TABLE 1

Minimal medium composition (PC1)

| Compound | Concentration |
| --- | --- |
| ZnSO$_4$·7H$_2$O | 0.0040 g · L$^{-1}$ |
| CuCl$_2$·2H$_2$O | 0.0020 g · L$^{-1}$ |
| MnSO$_4$·H$_2$O | 0.0200 g · L$^{-1}$ |
| CoCl$_2$·6H$_2$O | 0.0080 g · L$^{-1}$ |
| H$_3$BO$_3$ | 0.0010 g · L$^{-1}$ |
| Na$_2$MoO$_4$·2H$_2$O | 0.0004 g · L$^{-1}$ |
| MgSO$_4$·7H$_2$O | 1 g · L$^{-1}$ |
| Citric acid | 6 g · L$^{-1}$ |
| CaCl$_2$·2H$_2$O | 0.04 g · L$^{-1}$ |
| K$_2$HPO$_4$·3H$_2$O | 10.5 g · L$^{-1}$ |
| Na$_2$HPO$_4$ | 2 g · L$^{-1}$ |
| (NH$_4$)$_2$HPO$_4$ | 8 g · L$^{-1}$ |
| NH$_4$Cl | 0.13 g · L$^{-1}$ |
| NaOH 4M | Adjusted to pH 6.8 |
| FeSO$_4$, 7H$_2$O | 0.04 g · L$^{-1}$ |
| Thiamine | 0.01 g · L$^{-1}$ |
| Glucose | 10 g · L$^{-1}$ |
| Ammonium thiosulfate | 5.6 g · L$^{-1}$ |
| Vitamin B12 | 0.01 g · L$^{-1}$ |
| MOPS | 5 g · L$^{-1}$ |
| IPTG | 0.0024 g · L$^{-1}$ |

As can be seen in table 2 the methionine/glucose yield ($Y_{met}$) is increased upon overexpression of cysJIH and cysPUWAM. The deletion of the pyruvate kinase encoding alleles pykA and pykF can further increase methionine/glucose yield. The deletion of the formyl-THF deformylase encoded by the purU gene further boosts methionine/glucose yield. Additional further expression of the metF gene by the construct Ptrc36-ARNmst17-metF still gives higher methionine/glucose yield. The overexpression of serA serC and serB even further increase methionine/glucose yield and the additional expression of glyA still increases the methionine/glucose yield.

TABLE 2

Methionine yield (Ymet) in % g methionine/g glucose produced in batch culture by strains described above. n.d., not determined. For the precise definition of methionine/glucose yield see below. SD denotes the standard deviation for Ymet.

| Genotype | Ymet | SD | Y homolanthionine |
| --- | --- | --- | --- |
| strain1 | 6.65 | 0.25 | nd |
| strain1 PtrcF-cysPUWAM PtrcF-cysJIH | 8.53 | 0.4 | 3.10 |
| strain1 PtrcF-cysPUWAM PtrcF-cysJIH ΔpykF ΔpykA | 10.16 | 0.27 | 1.98 |
| strain1 PtrcF-cysPUWAM PtrcF-cysJIH ΔpykF ΔpykA Ptrc09-gcvTHP | 10.14 | 0.44 | 1.82 |
| strain1 PtrcF-cysPUWAM PtrcF-cysJIH ΔpykF ΔpykA Ptrc09-gcvTHP ΔpurU | 10.33 | 0.06 | 0.71 |
| strain1 PtrcF-cysPUWAM PtrcF-cysJIH ΔpykF ΔpykA Ptrc09-gcvTHP Ptrc36-ARNmst17-metF | 9.68 | 1.1 | 0.8 |
| strain1 PtrcF-cysPUWAM PtrcF-cysJIH ΔpykF ΔpykA Ptrc09-gcvTHP ΔpurU Ptrc36-ARNmst17-metF | 10.83 | 0.73 | 0.8 |

TABLE 2-continued

Methionine yield (Ymet) in % g methionine/g glucose produced in batch culture by strains described above. n.d., not determined. For the precise definition of methionine/glucose yield see below. SD denotes the standard deviation for Ymet.

| Genotype | Ymet | SD | Y homolanthionine |
|---|---|---|---|
| strain1 PtrcF-cysPUWAM PtrcF-cysJIH ΔpykF ΔpykA Ptrc09-gcvTHP (pJB137-lpd) | 9.75* | nd | 0.3* |
| strain1 PtrcF-cysPUWAM PtrcF-cysJIH ΔpykF ΔpykA Ptrc09-gcvTHP ΔpurU Ptrc36-ARNmst17-metF (pCC1BAC serB-serA-serC) | 12.54 | 0.19 | 0.1 |
| strain1 PtrcF-cysPUWAM PtrcF-cysJIH ΔpykF ΔpykA Ptrc09-gct/THP ΔpurU Ptrc36-ARNmst17-metF (pCC1BAC-serB-glyA serA-serC) | 12.85 | 0.44 | 0.14 |

* test performed with 5g/l glucose in final culture.

Determination of Changes in Enzyme Activities of CysM, cysJI, PykA/F, GcvTHP and lpd, serA, serB, serC and glyA To validate the changes in the expression of CysM, CysJI, PykA/F, GcvTHP, SerA, SerB, SerC, GlyA and Lpd the activities of the corresponding enzymes were determined in crude extracts.

For the determination of enzyme activities in vitro, $E.\ coli$ strains were cultured in minimal medium as described above and harvested at mid log phase. Cells were suspended in cold potassium phosphate buffer and sonicated on ice (Branson sonifier, 70 W). In two cases (shown in grey cases in table 3), proteins were extracted by using a precellys extraction system (Bertin technologies, France): Cells were suspended in cold potassium phosphate buffer, mixed with 0.1 mm glass beads and extracted with one run of 30 s. After centrifugation, proteins contained in the supernatants were quantified (Bradford, 1976).

Sulfocysteine synthase activity (CysM) was assayed by LC-MS quantification of the produced sulfocysteine. For the test 25 µg/mL of protein were placed in a potassium phosphate buffer (0.5 M, pH 6.5) containing 25 mM of 0-acetylserine and 25 mM thiosulfate. The reaction was run for 10 minutes at 30° C., and further processed for LC-MS quantification.

Sulfite reductase activity (CysJI) was assayed by the disappearance of NADPH. The reaction mixture was composed of 10 mM sodium hydrogensulfite and 10 mM NADPH in Tris-HCl (0.5 M, pH 7.5). The reaction was started by adding 30 µL of protein extract and followed at 340 nm for 30° C. min in a thermostated spectrophotometer.

For the determination of pyruvate kinase activity (PykA/F), a lactate dehydrogenase (LDH) coupled assay was performed. 10 µL of protein extract were added to a solution buffered with Tris-HCl (0.5 M, pH 7.5) containing 10 mM DTT, 100 mM $MgCl_2$, 100 mM KCl, 10 mM PEP, 50 mM AMP, 10 mM fructose 1,6 bis phosphate, 10 mM NADH and 10 units of LDH. The reaction was followed at 340 nm at 30° C. for 30 min in a thermostated spectrophotometer.

The activity of GcvTHP, components of the Glycine Cleavage Complex, was estimated by measuring $CO_2$ production occurring during the glycine decarboxylation reaction. The reaction was performed in a sided arm Warburg flask containing 0.5 M potassium phosphate buffer at pH 7.2 mM, pyridoxal phosphate, 200 mM lipoamide and 1-14C-glycine 1M at 50 µCi/mL. 400 µL of hyamine were placed in the center well of the flask and the whole reaction system was pre-incubated 5 mM at 37° C. The enzymatic reaction was started by adding 2 mg of protein and run at 37° C. It was stopped by adding through the septum of the sided arm 500 µL of 6N $H_2SO_4$, and 14C—$CO_2$ was trapped by the hyamine by incubating for another hour at 37° C. The liquid in the center well was then removed and added to 3 mL of scintillation liquid before determining CPM in a scintillation counter.

Methylene tetrahydrofolate reductase activity (MTHFR, MetF) was determined by derivatization of the radioactive demethylated methyl carrier. The reaction mixture contained potassium phosphate (50 mM, pH 6.7), 0.02% BSA (solution at 2% BSA in 30 mM EDTA), 37.5 µM FAD, 140 µM menadione and 300 µM 5-14C-Methyl-THF at 925 dpm/nmol. After a 5 min preincubation at 37° C., 100 µL of protein extract at 1 µg of protein/µL were added. The reaction was run for 15 min at 37° C. and stopped by adding 300 µL of a 3 mg/mL dimedone solution in sodium acetate (1M, pH 4.7). The reaction solution was then incubated 2 min at 100° C. and cooled off on ice for 5 min. 3 mL of toluene were then added and the reaction solution was centrifuged for 5 min at 1500 g at room temperature. 1.5 mL of the aqueous phase were taken and added to 3 mL of scintilliation liquid. The CPM were determined with a scintilliation counter and the activity calculated.

Lipoamide dehydrogenase activity of Lpd was determined based on the reduction of lipoamide with NADH as the electron donor. EDTA 10 mM, NADH 1 mM and $NAD^+$ 25 mM and 1 µg of protein extract were added to a Tris-HCl (0.5 M, pH 8.0) buffered solution. The reaction was started by adding 200 mM of lipoamide and the NADH disappearance was followed at 340 nm at 30° C. for 30 min in a thermostated spectrophotometer.

Phosphoglycerate dehydrogenase activity of SerA was monitored by following the disappearance of NADH. 30 µl of protein extract were placed in Tris-HCl (10 mM, pH 8.8) solution containing 360 µM 3-P-hydroxypyruvate. 200 µM NADH were added to start the reaction and the disappearance of NADH was followed at 340 nm at 30° C. for 30 min in a thermostated spectrophotometer.

The phosphoserine phospatase activity carried by the SerB protein was determined by measuring the serine produced by GC-MS. The reaction mixture contained TEA-HCL (10 mM, pH 7.5), 1 mM MgCl2, 1 mM O-phospho-L-serine and 15 µg of protein. The reaction was incubated at 37° C. and stopped at 10 and 30 minutes by addition of acetone and further processed for GC-MS quantification.

Phosphophoserine-amino-transferase activity of SerC was measured by coupling the assay with glutamate dehydrogenase. The reaction mixture was buffered by Tris-HCl (50 mM, pH 8.2) and contained 32 mM ammonium acetate, 2 mM glutamate, 2 uts Glutamate Dehydrogenase, 200 µM NADH. The reaction was started by adding 30 µl, of protein extract and the disappearance of NADH was followed at 340 nm at 30° C. for 30 min in a thermostated spectrophotometer.

Serine hydroxymethyl transferase activity was measured by monitoring the glycine produced by GC-MS. 30 μg of protein were added to a solution containing potassium phosphate (50 mM, pH 7.3), 400 μM of tetrahydopteroyl glutamate, 10 mM L-serine and 500 μM DTT. The reaction was run 10 minutes at 37° C. and stopped after 10 minutes by addition of acetone and further processed for GC-MS quantification.

The preculture medium B1 contained only 50 mM phosphate to avoid introducing additional phosphate into the batch medium with the inoculum. To stop growth at a cellular concentration of 30 g·L$^{-1}$, phosphate was added to 28.7 mM added to the mineral medium B2. The fed batch media (F1 and F2) were phosphate free.

Briefly, an 8 hour culture grown in 10 mL LB medium with 2.5 g·L$^{-1}$ glucose was used to inoculate a 12 h precul-

TABLE 3

Activities shown are in mUI/mg protein for cysteine synthase B (CysM), sulfite reductase (CysJI), pyruvate kinase (PykA/F), methylene-tetrahydrofolate reductase (MetF), lipoamide dehydrogenase (Lpd), 3-phosphoglycerate dehydrogenase (SerA), phosphoserine phosphatise (SerB), phosphoserine-amino-transferase (SerC), serine hydroxymethyl transferase (GlyA) in methionine producing strains. Glycine decarboxylase activity of GcvTHP is in μU/mg of protein.. Activities marked in grey cases were obtained from cultures extracted on a Precellys system.

| Genotype | CysM | CysJI | PykA/F | gcvTHP | MetF | Ipd |
|---|---|---|---|---|---|---|
| strain1 | 54 | 13 | 162 | ND | ND | ND |
| strain1 PtrcF-cysPUWAM PtrcF-cysJIH | 318 | 18 | 216 | 10 | ND | ND |
| strain1 PtrcF-cysPUWAM PtrcF-cysJIH ΔpykF ΔpykA | ND | ND | <LOQ | 12 | ND | ND |
| strain1 PtrcF-cysPUWAM PtrcF-cysJIH ΔpykF ΔpykA Ptrc09-gcvTHP | 514 | ND | <LOQ | 19 | 7 | 592 |
| strain1 PtrcF-cysPUWAM PtrcF-cysJIH ΔpykF ΔpykA Ptrc09-gcvTHP Ptrc36-ARNmst17-metF | ND | ND | ND | ND | 53 | ND |
| strain1 PtrcF-cysPUWAM PtrcF-cysJIH ΔpykF ΔpykA Ptrc09-gcvTHP (pJ B137-lpd) | ND | ND | ND | ND | ND | 1626 |
| | SerA | SerB | SerC | GlyA | | |
| strain1 PtrcF-cysPUWAM PtrcF-cysJIH ΔpykF ΔpykA Ptrc09-gcvTHP ΔpurU Ptrc36-ARNmst17-metF | 22 | 46 | 39 | 341 | | |
| strain1 PtrcF-cysPUWAM PtrcF-cysJIH ΔpykF ΔpykA Ptrc09-gcvTHP ΔpurU Ptrc36-ARNmst17-metF (pCC1BAC-serA-serC) | 47 | ND | 70 | ND | | |
| strain1 PtrcF-cysPUWAM PtrcF-cysJIH ΔpykF ΔpykA Ptrc09-gcvTHP ΔpurU Ptrc36-ARNmst17-metF (pCC1BAC serB-serA-serC) | 50 | 217 | 88 | 598 | | |
| strain1 PtrcF-cysPUWAM PtrcF-cysJIH ΔpykF ΔpykA Ptrc09-gcvTHP ΔpurU Ptrc36-ARNmst17-metF | 43 | 10 | 45 | 279 | | |
| strain1 PtrcF-cysPUWAM PtrcF-cysJIH ΔpykF ΔpykA Ptrc09-gcvTHP ΔpurU Ptrc36-ARNmst17-metF (pCC1BAC-serB-glyA-serA-serC) | 87 | 48 | 75 | 715 | | |

LOQ: limit of quantification; ND: not determined

As can be seen from table 3 the constructs PtrcF-cysPUWAM, PtrcF-cysJIH Ptrc09-gcvTHP and Ptrc39-ARNmst17-metF, pJB137-lpd, pCC1BAC-serB-serA-serC and pCC1BAC-serB-glyA-serA-serC all increase the activity of the corresponding enzyme when compared to the strain not modified for the corresponding allele. Deletion of pykA and pykF leads to a complete loss of pyruvate kinase activity.

Validation of Methionine Production Under Fermentation Conditions

Strains that produced substantial amounts of metabolites of interest were subsequently tested under production conditions in 2.5 L fermentors (Pierre Guerin) using a fed batch strategy with phosphate starvation.

ture in minimal medium (B1 without ammonium thiosulfate but with MOPS 5 g·L$^{-1}$). These incubations were carried out in 500 mL baffled flasks containing 50 mL of minimal medium (B1) in a rotary shaker (200 RPM) at 37° C.

A third preculture step was carried out in bio-reactors (Sixfors) filled with 200 mL of minimal medium (B1) inoculated to a biomass concentration of 0.05 g·L$^{-1}$ with 1.5 mL concentrated preculture (5 g·L$^{-1}$). The preculture temperature was maintained constant at 37° C. and the pH was automatically maintained at a value of 6.8 using a 10% NH$_4$OH solution. The dissolved oxygen concentration was continuously adjusted to a value of 30% of the partial air pressure saturation with air supply and/or agitation. After glucose exhaustion from the batch medium, the fed batch was started with an initial flow rate of 0.7 mL·h$^{-1}$, increased exponentially for 24 hours with a growth rate of 0.18 h$^{-1}$ in order to obtain a final cellular concentration of about 24 g·L$^{-1}$.

TABLE 4

Preculture batch mineral medium composition (B1)

| Compound | Concentration (g · L$^{-1}$) |
|---|---|
| Zn(CH$_3$COO)$_2$, 2H$_2$O | 0.0130 |
| CuCl$_2$, 2H$_2$O | 0.0015 |
| MnCl$_2$, 4H$_2$O | 0.0150 |
| CoCl$_2$•6H$_2$O | 0.0025 |
| H$_3$BO$_3$ | 0.0030 |
| Na$_2$MoO$_4$•2H$_2$O | 0.0025 |
| MgSO$_4$•7H$_2$O | 1 |
| CaCl$_2$ | 0.0800 |
| Citric acid | 1.7000 |
| KH$_2$PO$_4$ | 4.50 |
| K$_2$HPO$_4$, 3H$_2$O | 2.50 |
| (NH$_4$)$_2$HPO$_4$ | 1.10 |
| (NH$_4$)$_2$SO$_4$ | 4.90 |
| Fe(III) citrate H$_2$O | 0.1064 |
| (NH$_4$)$_2$S$_2$O$_3$ | 1 |
| EDTA | 0.0084 |
| Thiamine | 0.01 |
| Glucose | 5 |
| Vitamin B12 | 0.01 |
| NaOH 8 N | Adjusted to pH 6.8 |

TABLE 5

Preculture fed-batch mineral medium composition (F1)

| Compound | Concentration (g · L$^{-1}$) |
|---|---|
| Zn(CH$_3$COO)$_2$•H$_2$O | 0.0104 |
| CuCl$_2$•2H$_2$O | 0.0012 |
| MnSO$_4$•H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| MgSO$_4$ | 5 |
| (NH$_4$)$_2$SO$_4$ | 8.30 |
| Na$_2$SO$_4$ | 8.90 |
| Fe(III) citrate H$_2$O | 0.0524 |
| (NH$_4$)$_2$S$_2$O$_3$ | 24.80 |
| EDTA | 0.0067 |
| Thiamine | 0.01 |
| Glucose | 500 |
| Vitamin B12 | 0.01 |
| NH$_4$OH 28% | Adjusted to pH 6.8 |

TABLE 6

Culture batch mineral medium compositions (B2 and B3)

| Compound | Concentration (g · L$^{-1}$) B2 | Concentration (g · L$^{-1}$) B3 |
|---|---|---|
| Zn(CH$_3$COO)$_2$•2H$_2$O | 0.0130 | 0.0130 |
| CuCl$_2$•2H$_2$O | 0.0015 | 0.0015 |
| MnCl$_2$•4H$_2$O | 0.0150 | 0.0150 |
| CoCl$_2$•6H$_2$O | 0.0025 | 0.0025 |
| H$_3$BO$_3$ | 0.0030 | 0.0030 |
| Na$_2$MoO$_4$•2H$_2$O | 0.0025 | 0.0025 |
| MgSO$_4$•7H$_2$O | 1 | 1 |
| CaCl$_2$•2H$_2$O | 0.0800 | 0.0800 |
| Citric acid | 1.70 | 1.70 |
| KH$_2$PO$_4$ | 2.50 | 16.42 |
| K$_2$HPO$_4$•3H$_2$O | 1.38 | 9.12 |
| (NH$_4$)$_2$HPO$_4$ | 0.6040 | 4 |
| Fe(III) citrate H$_2$O | 0.11 | 0.11 |
| (NH$_4$)$_2$S$_2$O$_3$ | 3.70 | 4.88 |
| EDTA | 0.0080 | 0.0080 |
| Thiamine | 0.01 | 0.01 |
| Glucose | 10 | 10 |
| Vitamin B12 | 0.01 | 0.01 |
| NaOH 8 N | Adjusted to pH 6.8 | Adjusted to pH 6.8 |
| IPTG | 0.0024 | 0.0024 |

TABLE 7

Culture Fed batchmedium composition (F2)

| Compound | Concentration (g · L$^{-1}$) |
|---|---|
| Zn(CH$_3$COO)$_2$, 2H$_2$O | 0.0104 |
| CuCl$_2$, 2H$_2$O | 0.0012 |
| MnCl$_2$, 4H$_2$O | 0.0120 |
| CoCl$_2$•6H$_2$O | 0.0020 |
| H$_3$BO$_3$ | 0.0024 |
| Na$_2$MoO$_4$•2H$_2$O | 0.0020 |
| Fe(III) citrate H$_2$O | 0.0524 |
| MgSO$_4$ | 5.0000 |
| (NH$_4$)$_2$S$_2$O$_3$ | 39.0900 |
| EDTA | 0.0067 |
| Thiamine | 0.0100 |
| Glucose | 500.0000 |
| Vitamin B12 | 0.0100 |
| IPTG | 0.0190 |

Subsequently 2.5 L fermentors (Pierre Guerin) were filled with 600 mL of minimal medium (B2) and were inoculated to a biomass concentration of 2.1 g·L$^{-1}$ with a preculture volume ranging from 45 to 60 mL.

The culture temperature was maintained constant at 37° C. and pH was maintained to the working value (6.8) by automatic addition of NH$_4$OH solutions (NH$_4$OH 10% for 10 hours and 24% until the culture end). The initial agitation rate was set at 200 rpm during the batch phase and was increased to up to 1000 rpm during the fed-batch phase. The initial airflow rate was set at 40 NL·h$^{-1}$ during the batch phase and was increased to 100 NL·h$^{-1}$ at the beginning of the fed-batch phase. The dissolved oxygen concentration was maintained at values between 20 and 40%, preferentially 30% saturation by increasing the agitation.

When the cell mass reached a concentration close to 5 g·L$^{-1}$, the fed batch was started with an initial flow rate of 5 mL·h$^{-1}$. Feeding solution was injected with a sigmoid profile with an increasing flow rate that reached 21 mL·h$^{-1}$ after 21 hours. The precise feeding conditions were calculated by the equation:

$$Q(t) = p1 + \frac{p2}{1 + e^{-p3(t-p4)}}$$

where Q(t) is the feeding flow rate in mL·h$^{-1}$ for a batch volume of 600 mL with p1=1.15, p2=18.32, p3=0.270, p4=5.

After 21 hours fed batch, the cellular concentration attained 30 g·L$^{-1}$ phosphate was depleted from the medium and cells entered phosphate starvation. At that point, injection of feeding solution was increased to a constant value of 37 mL·h$^{-1}$ for 4 hours. Then, the constant flow rate was decreased to 10 mL·h$^{-1}$ and this flow value was maintained until the end of the fed batch (50 hours).

TABLE 8

Maximum methionine/glucose yield (NAM was counted as methionine, % g/g see below) obtained in Fed-batch fermentations of strains described above. For the precise definition of methionine/glucose yield see below.

| Genotype | $Y_{met+NAM}$ | $Y_{iso}$ | $Y_{homolanthionine}$ |
|---|---|---|---|
| strain1 PtrcF-cysPUWAM PtrcF-cysJIH ΔpykF ΔpykA Ptrc09-gcvTHP | 14.4 ± 1 | 1.3 ± 0.5 | 2.8 ± 0.03 |
| strain1 PtrcF-cysPUWAM PtrcF-cysJIH ΔpykF ΔpykA Ptrc09-gcvTHP ΔpurU | 15.6 ± 1.2 | 1.7 ± 0.4 | 0.93 ± 0.13 |
| strain1 PtrcF-cysPUWAM PtrcF-cysJIH ΔpykF ΔpykA Ptrc09-gcvTHP ΔpurU (pCC1BAC-serA-serC) | 17.2 ± 1.4 | 0.29 ± 0.05 | 0.47 ± 0.05 |
| strain1 PtrcF-cysPUWAM PtrcF-cysJIH ΔpykF ΔpykA Ptrc09-gcvTHP ΔpurU Ptrc36-ARNmst17-metF | 17.4 ± 0.9 | 2.3 ± 0.15 | 0.81 ± 0.3 |
| strain1 PtrcF-cysPUWAM PtrcF-cysJIH ΔpykF ΔpykA Ptrc09-gcvTHP ΔpurU Ptrc36-ARNmst17-metF (pCC1BAC serB-serA-serC) | 19.2 ± 1.6 | 0.105 ± 0.183 | 0.16 ± 0.05 |
| strain1 PtrcF-cysPUWAM PtrcF-cysJIH ΔpykF ΔpykA Ptrc09-gcvTHP ΔpurU Ptrc36-ARNmst17-metF (pCC1BAC-serA-serC) | 18.2 ± 1.9 | 1 ± 0.6 | 0.1 ± 0.02 |
| strain1 PtrcF-cysPUWAM PtrcF-cysJIH ΔpykF ΔpykA Ptrc09-gcvTHP ΔpurU Ptrc36-ARNmst17-metF (pCC1BAC-serB-glyA-serA-serC) | 19.9 ± 0.9 | 0.64 ± 0.29 | 0.07 ± 0.03 |

As can be seen from table 8 the deletion of the purU gene significantly increases the methionine/glucose yield. Isoleucine production is significantly reduced by overexpressing serA serC from pCC1BAC-serA-serC. Additional further expression of the serB gene further decreases isoleucine production and increases the methionine/glucose yield.

Determination of Methionine/Glucose Yield ($Y_{met}$)

Extracellular methionine concentration was quantified by HPLC after OPA/FMOC derivatization. The NAM concentration and residual glucose concentration was analyzed using HPLC with refractometric detection. The methionine yield was expressed as followed:

$$Y_{met} = \frac{\text{methionine(g)}}{\text{consummed glucose(g)}} * 100$$

Batch Cultures:

In order to determine initial and final culture volumes, the Erlenmeyer flask was weighed empty, with the medium and at the end of the culture. The methionine yield was expressed as follows:

$$Y_{met} = \frac{\text{Methionine}_f * V_f - \text{Methionine}_0 * V_0}{\text{Glucose}_0 * V_0 - \text{Glucose}_f * V_f} * 100$$

With $\text{Methionine}_0$ and $\text{Methionine}_f$ respectively the initial and final methionine concentrations, $\text{Glucose}_0$ and $\text{Glucose}_f$ respectively the initial and final glucose concentrations and $V_0$ and $V_f$ the initial and final volumes.

Fed Batch Cultures:

The fermentor volume was calculated by adding to the initial volume the amount of solutions added to regulate the pH and to feed the culture and by subtracting the volume used for sampling and lost by evaporation.

The fed batch volume was followed continuously by weighing the feeding stock. The amount of injected glucose was then calculated on the basis of the injected weight, the density of the solution and the glucose concentration determined by the method of Brix ([Glucose]). The methionine yield was expressed as followed:

$$Y_{met} = \frac{\text{Methionine}_t * V_t - \text{Methionine}_0 * V_0}{\text{Consumed glucose}_t} * 100$$

With $\text{Methionine}_0$ and $\text{Methionine}_t$ respectively the initial and final methionine concentrations and $V_0$ and $V_t$ the initial and the instant t volumes.

The consumed glucose was calculated as follows:

$$\text{fed volume}_t = \frac{\text{fed weight}_0 - \text{fed weight}_t}{\text{density fed solution}}$$

Injected Glucose$_t$=fed volume$_s$*[Glucose]

Consumed glucose$_t$=[Glucose]$_0$*$V_0$+Injected Glucose−[Glucose]$_{residual}$*$V_t$ With [Glucose]$_o$, [Glucose], [Glucose]$_{residual}$ respectively the initial, the fed and the residual glucose concentrations.

Phosphate Limitation or Starvation Increases Methionine/Glucose Yield

In order to demonstrate that phosphate limitation and also phosphate starvation increases the methionine/glucose yield fed batch fermentations were performed as described above. For the culture without phosphate starvation or limitation, the mineral medium B3 was used and the fed batch medium was F2 completed with Na2SO4 (8.95.L-1) and (NH4)2SO4 (8.32 g·L-1). For the culture grown under phosphate limitation the following modifications were introduced. The batch mineral medium used was B2 and the fed batch medium was F2 completed with 60 mM of phosphate. The phosphate limitation occurred at an OD600 nm of 100.

Figure 2:
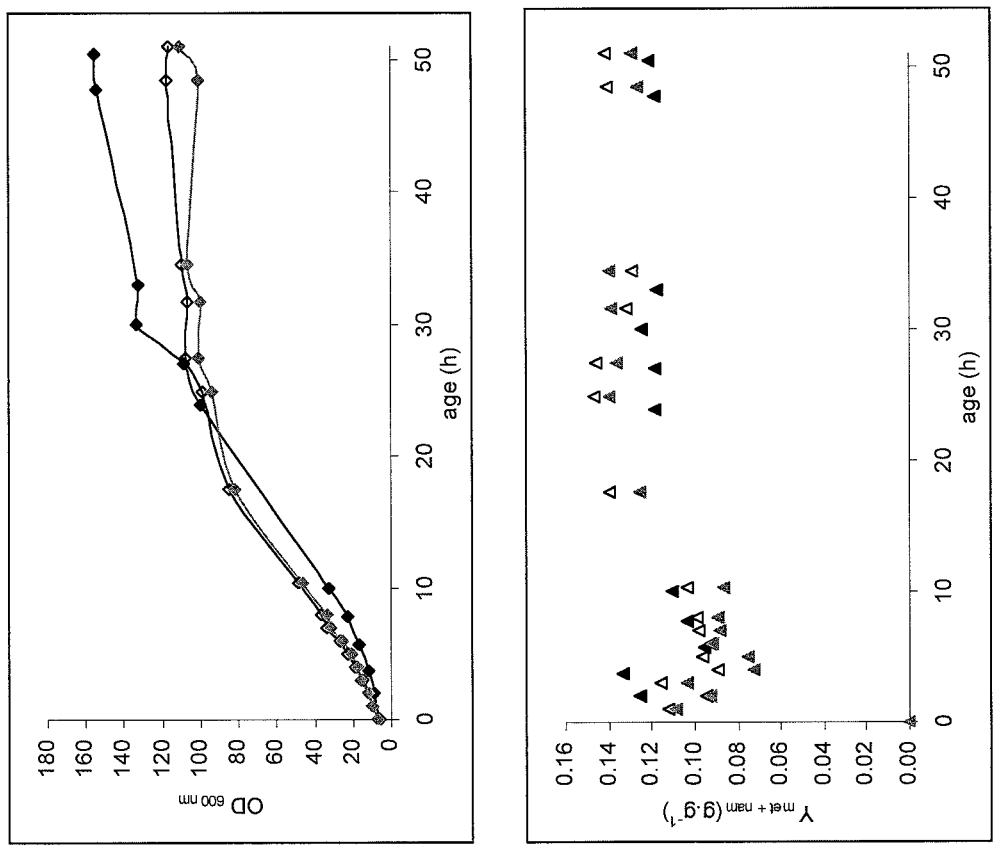

As can be seen from FIG. 2 under phosphate excess the $OD_{600\ nm}$ increased continuously during the culture and attained 160 UOD at the end of the experiment. In the case of phosphate limitation and starvation the cellular growth rate decreased starting from an $OD_{600\ nm}$ of 100 (20 hours) and the final $OD_{600\ nm}$ was close to 120. The residual phosphate concentration was close to zero, which was confirmed by ionic chromatography. As a consequence of the phosphate starvation and limitation the methionine yield increased and attained the maximal value of 0.147 and 0.139 g·g$^{-1}$, respectively, compared to 0.124 g·g$^{-1}$ under phosphate excess.

The invention claimed is:

1. A method for the production of methionine in a fermentative process comprising the following steps:
culturing a modified microorganism in an appropriate culture medium comprising a source of carbon and sulfate, thiosulfate, or a mixture of both as a source of sulfur, and recovering methionine from the culture medium, wherein said modified microorganism is a genetically modified *E. coli* comprising
a deleted methionine repressor gene metJ,
an overexpressed metA gene coding homoserine succinyltransferase alleles with reduced feed-back sensitivity to S-adenosylmethionine and/or methionine,
an overexpressed thrA gene coding for alleles of aspartokinase/homoserine dehydrogenase with reduced feed-back inhibition to threonine,
an overexpressed metF gene coding for a 5,10-methylenetetrahydrofolate reductase,
an overexpressed metH gene coding for a B12-dependent homocysteine-N5-methyltetrahydrofolate transmethylase,
an overexpressed cysE gene coding for a serine acetyltransferase,
an overexpressed cysPUWAMoperon coding a sulfate/thiosulfate importer and a thiosulfate specific cysteine synthase,
an overexpressed cysJIH operon coding a sulfite reductase and a phosphoadenylyl-sulfate (PAPS) reductase, and
an overexpressed gvcTHPoperon coding a glycine cleavage complex,
wherein, compared to the non-modified microorganism, said modified microorganism presents
a decreased deformylation of formyl-tetrahydrofolate (formyl-THF) obtained by deletion of a purU gene coding a formyl-THF deformylase and
a reduction of the consumption of phosphoenol pyruvate (PEP) by attenuating the expression of or deletion of a pykA gene coding a pyruvate kinase and/or a pykF gene coding a pyruvate kinase
wherein the growth and biomass production of the said modified microorganism is limited by limiting or starving said modified microorganism for phosphate in the culture medium.

2. The method of claim 1, wherein the source of carbon in said culture medium is selected from the group consisting of hexoses, pentoses, monosaccharides, disaccharides, oligosaccharides, molasses, starch or its derivatives, hemicelluloses, glycerol, and combinations thereof.

3. The method of claim 2 wherein the carbon source is glucose or sucrose.

4. The method of claim 1, wherein the genetically modified *E. coli* comprises Ptrc36-ARNmst17-metF coding a 5,10-methylene tetrahydrofolate (THF) reductase.

* * * * *